(12) United States Patent  
Wagner et al.

(10) Patent No.: US 7,387,777 B2  
(45) Date of Patent: Jun. 17, 2008

(54) METHODS OF TREATING HEMOPHILIA OR VON WILLEBRAND DISEASE WITH P-SELECTIN

(75) Inventors: Denisa D. Wagner, Wellesley, MA (US); Patrick Andre, Jamaica Plain, MA (US); Daqing W. Hartwell, Brookline, MA (US); Ingrid Hrachovinova, Jamaica Plain, MA (US)

(73) Assignee: Center For Blood Research, Inc., Boston, MA (US)

( * ) Notice: Subject to any disclaimer, the term of this patent is extended or adjusted under 35 U.S.C. 154(b) by 502 days.

(21) Appl. No.: 10/782,456

(22) Filed: Feb. 19, 2004

(65) Prior Publication Data

US 2004/0265311 A1     Dec. 30, 2004

Related U.S. Application Data

(62) Division of application No. 09/860,618, filed on May 17, 2001.

(60) Provisional application No. 60/205,734, filed on May 19, 2000.

(51) Int. Cl.
*A61K 35/12* (2006.01)
*C07K 14/435* (2006.01)

(52) U.S. Cl. ............... 424/134.1; 424/192.1; 514/8; 530/350; 530/387.3

(58) Field of Classification Search ............... None
See application file for complete search history.

(56) References Cited

U.S. PATENT DOCUMENTS

| | | | | |
|---|---|---|---|---|
| 5,378,464 | A * | 1/1995 | McEver | 424/143.1 |
| 5,510,102 | A * | 4/1996 | Cochrum | 424/78.08 |
| 5,622,701 | A | 4/1997 | Berg | 424/153.1 |
| 5,800,815 | A | 9/1998 | Chestnut et al. | 424/153.1 |
| 5,807,745 | A | 9/1998 | Furie et al. | 435/375 |
| 5,840,679 | A * | 11/1998 | Larsen et al. | 514/2 |
| 5,843,707 | A | 12/1998 | Larsen et al. | 435/69.1 |
| 6,033,667 | A | 3/2000 | Chesnut et al. | 424/153.1 |
| 6,277,675 | B1 * | 8/2001 | Tung | 438/138 |
| 6,596,705 | B1 * | 7/2003 | Varki et al. | 514/56 |

FOREIGN PATENT DOCUMENTS

WO    WO 93/06863 A1    4/1993

OTHER PUBLICATIONS

Grunewald et al., Trends in Molecular Medicine 10: 9-10, 2004.*
Skolnick et al., Trends in Biotech. 18(1):34-38, 2000.*
Krause et al., Clinical & Experimental Metastasis 17: 183-192, 1999.*
GenBank Acc. No. NM_003005 for *Homo sapiens* selectin P (granule membrane protein 140kD, antigen CD62) (SELP), mRNA, Feb. 3, 2001.
GenBank Acc. No. M25322 for Human granule membrane protein-140 mRNA, complete cds, Apr. 27, 1993.
GenBank Acc. No. NM_013114 for Rattus norvegicus Selectin, platelet (Selp), mRNA, Nov. 1, 2000.
GenBank Acc. No. L23088 for Rattus norvegicus P-selectin mRNA, complete cds, Nov. 10, 1995.
GenBank Acc. No. NM_011347 for Mus musculus selectin, platelet (Selp), mRNA, Nov. 1, 2000.
GenBank Acc. No. M87861 for Mus musculus P-selectin protein mRNA, complete cds, Apr. 27, 1993.
GenBank Acc. No. L12041 for Bovine P-selectin mRNA, complete cds, Feb. 26, 1993.
Andre, P. et al., "Pro-coagulant state resulting from high levels of soluble P-selectin in blood," *Proc Natl Acad Sci USA* 97(25):13835-40 (2000).
Auchampach, J.A., et al., "Cloning, sequence comparison and in vivo expression of the gene encoding rat P-selectin" *Gene* 145 (2), 251-255 (1994).
Berger, G. et al., "P-Selectin and platelet clearance," *Blood* 92(11):4446-52 (1998).
Bevilacqua, M., et al., "Selectins: a family of adhesion receptors," *Cell* 67 (2), 233 (1991).
Borsig, L. et al., "Heparin and cancer revisited: Mechanistic connections involving platelets, P-selectin, carcinoma mucins, and tumor metastasis," *Proc Natl Acad Sci USA* 98(6):3352-7 (2001).
Blann, A.D. et al., "Soluble P-selectin in atherosclerosis: a comparison with endothelial cell and platelet markers," *Thromb. Haemost.* 77(6):1077-80 (1997).
Celi, et al., "P-selectin induces the expression of tissue factor on monocytes," *Proc Natl Acad Sci USA* 91(19):8767-71 (1994).
Ertenli, I. et al., "P-selectin as a circulating molecular marker in rheumatoid arthritis with thrombocytosis," *J. Rheumatol.* 25(6):1054-8 (1998).
Ferroni, P. et al., "Soluble P-selectin as a marker of platelet hyperactivity in patients with chronic obstructive pulmonary disease," *J. Investig. Med.* 48(1):21-7 (2000).

(Continued)

Primary Examiner—Phillip Gambel
(74) Attorney, Agent, or Firm—Rissman Jobse Hendricks & Oliverio, LLP

(57) ABSTRACT

The present invention identifies P-selectin as a modulator of hemostasis. Accordingly, the present invention relates to methods for the identification and use of modulators of P-selectin activity as modulators of hemostasis. The invention also relates to methods and compositions for the diagnosis and treatment of hemostatic disorders, including, but not limited to, hemorrhagic disorders and thrombotic disorders. The present invention describes methods for the diagnostic evaluation and prognosis of various hemostatic conditions, and for the identification of subjects exhibiting a predisposition to such conditions. In addition, the present invention provides methods for the diagnostic monitoring of patients undergoing clinical evaluation for the treatment of a hemostatic or vascular disorders, and for monitoring the efficacy of compounds in clinical trials.

7 Claims, 14 Drawing Sheets

OTHER PUBLICATIONS

Gurbel, P.A. et al., "Role of soluble and platelet-bound P-selectin in discriminating cardiac from noncardiac chest pain at presentation in the emergency department," *Am. Heart J.* 139(2 Pt 1):320-8 (2000).

Hartwell, D.W. et al., "Role of P-selectin cytoplasmic domain in granular targeting in vivo and in early inflammatory responses," *J. Cell Biol.* 143(4):1129-41 (1998).

Haznedaroglu, I.C. et al., "Selectins and IL-6 during the clinical course of idiopathic thrombocytopenic purpura," *Acta Haematol.* 101(1):16-20 (1999).

Inoue, T. et al., "Serum levels of circulating adhesion molecules after coronary angioplasty," *Cardiology*, 1999;91(4):236-42 (1999).

Ishiwata, N. et al., "Alternatively spliced isoform of P-selectin is present in vivo as a soluble molecule," *J. Biol. Chem.* 269(38):23708-15 (1994).

Johnston, G.I., et al., "Cloning of GMP-140, a granule membrane protein of platelets and endothelium: Sequence similarity to proteins involved in cell adhesion and inflammation," *Cell* 56;1033-1044 (1989).

Johnston, G.I., et al., "Structure of the human gene encoding granule membrane protein-140, a member of the selectin family of adhesion receptors for leukocytes," *J. Biol. Chem.* 265 (34), 21381-21385 (1990).

Kopp, H.P. et al., "Concentrations of circulating P-selectin are increased in patients with newly diagnosed insulin-dependent diabetes mellitus," *Exp. Clin. Endocrinol. Diabetes* 106(1):41-4 (1998).

Palabrica, T. et al., "Leukocyte accumulation promoting fibrin deposition is mediated in vivo by P-selectin on adherent platelets," *Nature* 359(6398):848-51 (1992).

Pan, J. et al., "Characterization of the promoter for the human P-selectin gene," *J. Biol. Chem.* 268 (30), 22600-22608 (1993).

Ridker, P.M. et al., "Soluble P-selectin and the risk of future cardiovascular events," *Circulation* 103:491-5 (2001).

Ryan, U.S. et al., "Cell-cell contact mechanisms," *Curr. Opin. Immunol.* 4(1), 33-37 (1992).

Sanders, W.E. et al., "Molecular cloning and analysis of in vivo expression of murine P-selectin," *Blood* 80(3):795-800 (1992).

Smith, A. et al., "Changes in the levels of soluble adhesion molecules and coagulation factors in patients with deep vein thrombosis," *Thromb. Haemost.* 82(6):1593-9 (1999).

Strubel, N.A., et al., "Isolation and characterization of a bovine cDNA encoding a functional homolog of human P-selectin," *Biochem. Biophys. Res. Commun.* 192, 338-344 (1993).

Weller, A., et al., "Cloning of the mouse endothelial selectins: Expression of both E- and P- selectin is inducible by tumor necrosis factor alpha," *J. Biol. Chem.* 267, 15176-15183 (1992).

Xu, D. et al., "Elevated plasma levels of soluble P-selectin in patients with acute myocardial infarction and unstable angina. An inverse link to lipoprotein(a)," *Int. J. Cardiol.* 64(3):253-8 (1998).

* cited by examiner

FIG. 2

Fibrin formation in a perfusion chamber
non anticoagulated blood, 212 s$^{-1}$, 2 minutes

| Genotype | Capillaries with Fibrin | Capillaries without Fibrin | n | | | Fibrin tail (μm) | |
|---|---|---|---|---|---|---|---|
| WT | 4 | 7 | 11 | ] p=.039 | | 11.25±0.9 | |
| P-sel-/- | 0 | 11 | 11 | ] p=.0001 | ] p=.021 | 0 | ] p<.0001 |
| Δct | 8 | 1 | 9 | | | 28.75±1.4 | |

FIG. 3

Hemorrhagic lesions in local Shwartzman reaction

|  | Genotype | | | |
|---|---|---|---|---|
|  | WT | Δct | WT + IgG1 | WT + s-P-Sel. |
| Macroscopic grading | 3.1±0.2 | 1.5±0.3 | 3±0.2 | 1.1±0.3 |
| Microscopic grading | └─ p=.001 ─┘ | | └─ p<.0001 ─┘ | |
| Hemorrhage | 3.5±0.2 | 2.1±0.3 | 2.5±0.3 | 0.8±0.2 |
|  | └─ p=.003 ─┘ | | └─ p<.0001 ─┘ | |
| Leuko. Infiltrate | 2.6±0.3 | 2.6±0.3 | 2.7±0.1 | 2±0.1 |
|  | └─ p=.4 ─┘ | | └─ p=.0002 ─┘ | |

Fibrin deposition in a local Shwartzman reaction

Data are representative of one experiment out of 4
independent determinations FSC, forward scatter, SSC, sideward scatter

| WT | Δct | Fold increase |
|---|---|---|
| 5910±597 n=4 | 11288±965 n=4 | 1.9 |
| WT+ IgG1 | WT+ s-P-sel | Fold increase |
| 7265±2056 n=3 | 19765±5130 n=3 | 2.7 |

FIG. 7
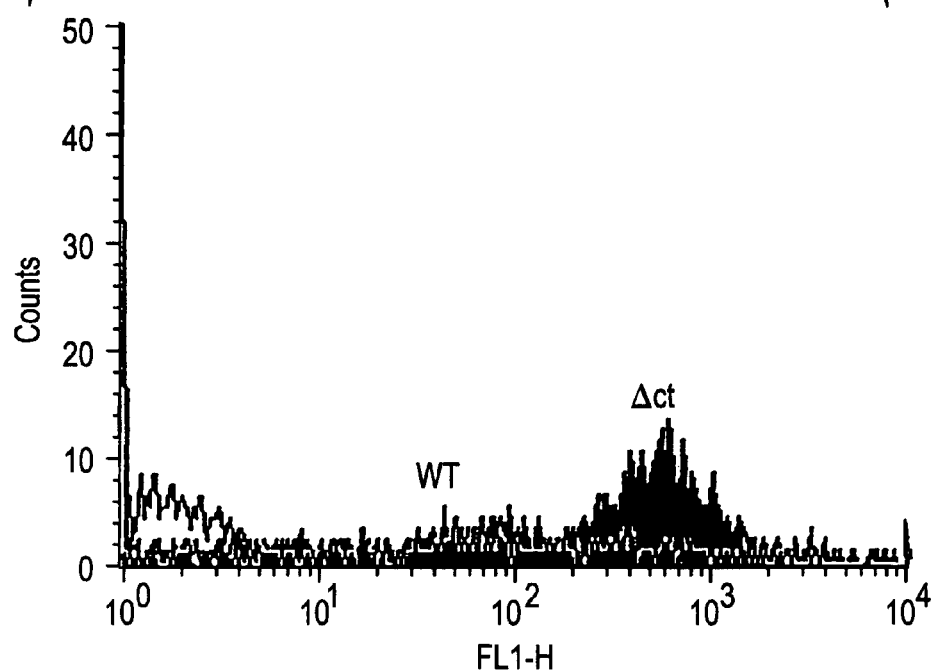
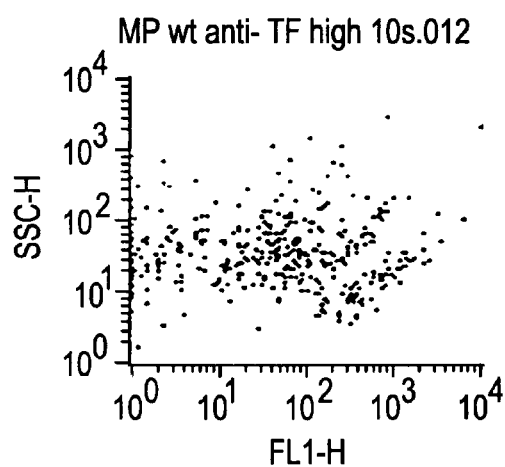
MP wt anti-TF high 10s.012
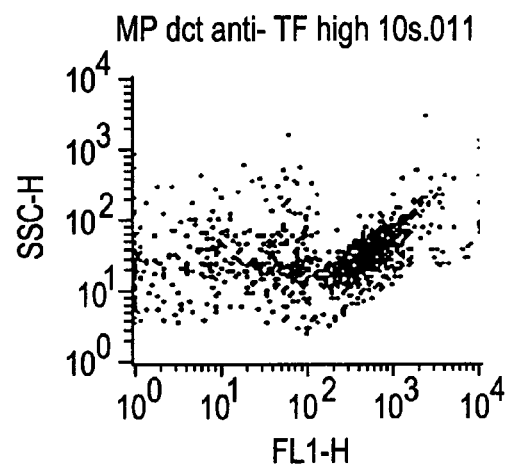
MP dct anti-TF high 10s.011

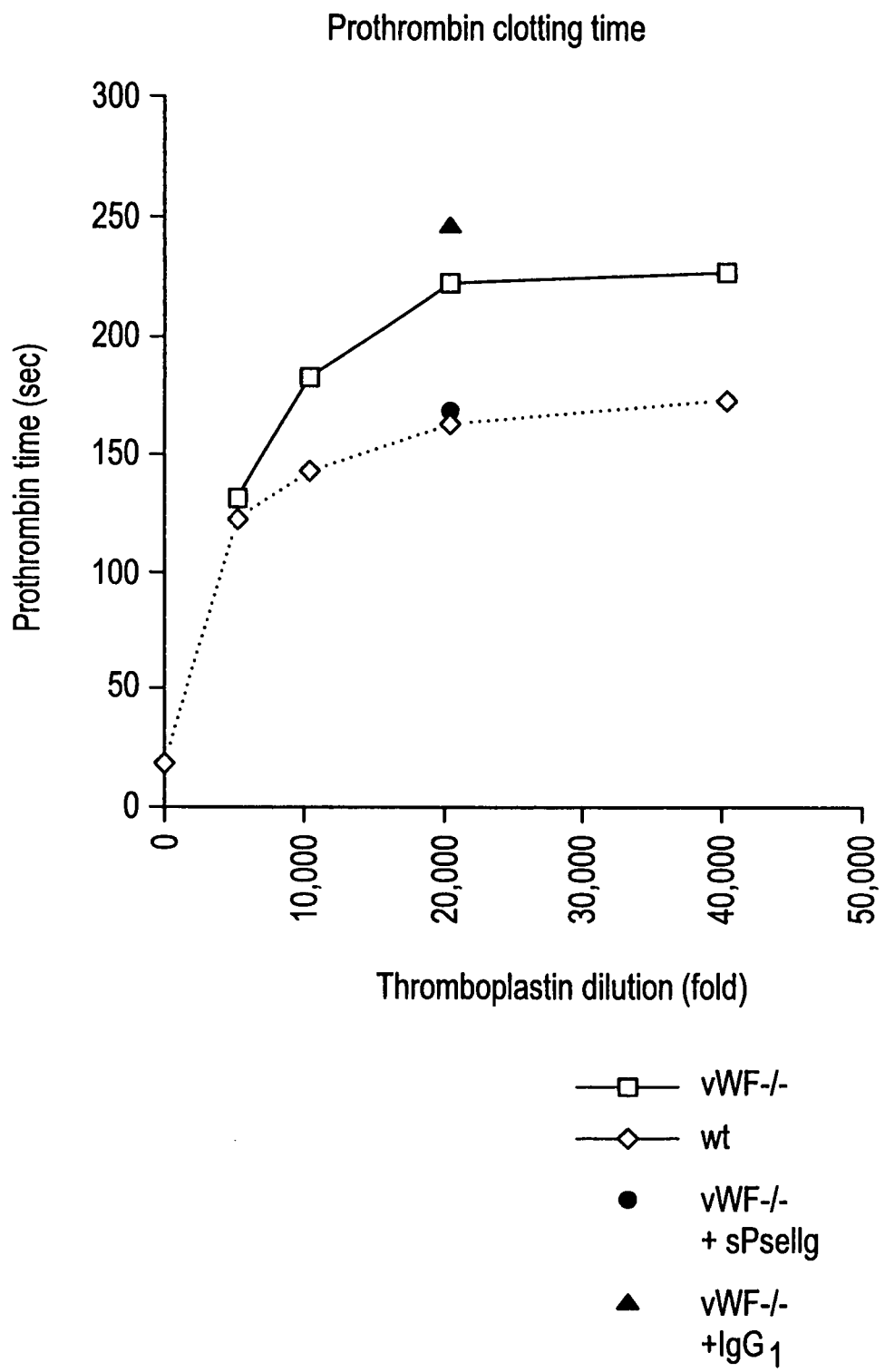

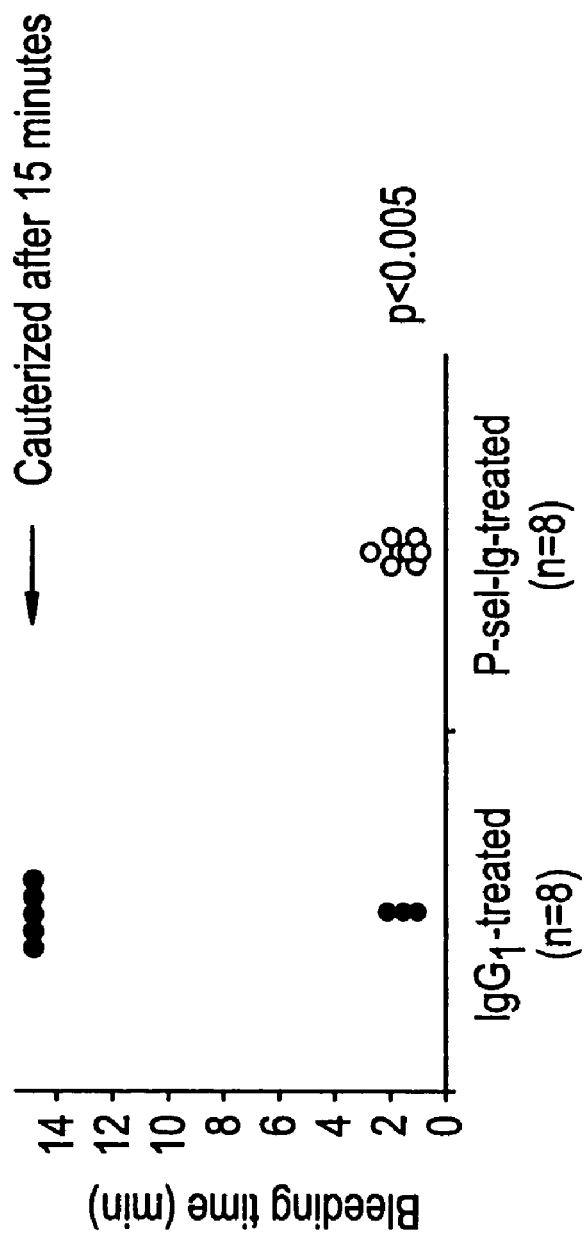

METHODS OF TREATING HEMOPHILIA OR VON WILLEBRAND DISEASE WITH P-SELECTIN

RELATED APPLICATIONS

This application is a divisional of U.S. application Ser. No. 09/860,618, filed May 17, 2001, which claims the benefit of prior-filed provisional patent application Ser. No. 60/205,734, filed May 19, 2000, entitled "Methods for Diagnosing and Treating Hemostatic Disorders By Modulating P-Selectin Activity". The entire content of the above-referenced provisional application is incorporated herein by this reference.

STATEMENT REGARDING FEDERALLY SPONSORED RESEARCH OR DEVELOPMENT

The invention described herein was supported, in whole or in part, by Grant No. P01-HL 56949 and Grant No. R01-HL53756 from the National Institutes of Health (NIH). The Government has certain rights in the invention.

BACKGROUND OF THE INVENTION

The ability of cells to adhere to one another plays a critical role in development, normal physiology, and disease processes. This ability is mediated by adhesion molecules, generally glycoproteins, expressed on the cell surface. Several important classes of adhesion molecules include the integrins, the selectins, and members of the immunoglobulin (Ig) superfamily. Selectins play a central role in mediating leukocyte adhesion to activated endothelium and platelets.

Blood clotting, along with inflammation and tissue repair, are host defense mechanisms which function in parallel to preserve the integrity of the vascular system after tissue injury. In response to tissue injury, platelets, endothelial cells and leukocytes are essential for the formation of a platelet plug, deposition of leukocytes in injured tissue, initiation of inflammation, and wound healing.

P-selectin, also known as CD62, granule membrane protein-140 (GMP-140), and platelet activation-dependent granule external membrane protein (PADGEM), is an integral membrane glycoprotein that is expressed on vascular endothelial cells and platelets, and is involved in the recognition of various circulating cells. The P-selectin molecule has an N-terminal lectin domain, a region with homology to epidermal growth factor, a region with homology to complement regulatory proteins, a transmembrane domain, and a short cytoplasmic tail. The P-selectin ligand includes the $Le^x$ carbohydrate structure, sialic acid, and the PSGL-1 protein (U.S. Pat. No. 5,843,707).

P-selectin is constitutively stored in secretory granules (e.g., α-granules and Weibel-Palade bodies) and is translocated to the surface of platelets and endothelial cells in response to a variety of stimuli, including cell activation, where it mediates platelet-leukocyte and endothelium-leukocyte interactions. The cell surface expression of P-selectin is tightly regulated, and P-selectin is rapidly shed from the cell surface upon platelet activation, appearing as a soluble fragment in the plasma (Berger, G. et al. *Blood* (1998)92:4446-4452). Soluble P-selectin may also result from an alternatively spliced isoform of P-selectin lacking the transmembrane domain (Ishiwata, N. et al. *J Biol Chem* (1994)269:23708). The plasma of healthy humans and mice contains little soluble P-selectin, as detected by ELISA, and an increase in plasma P-selectin concentration may indicate in vivo activation of and/or damage to platelets and endothelial cells.

In addition to its role in leukocyte rolling and extravasation in inflammation, P-selectin mediates platelet-leukocyte adhesion within thrombi, and increases tissue factor expression on monocytes, thereby promoting fibrin deposition by leukocytes and thrombogenesis (Palabrica, T. et al. *Nature* (1992) 359:848-851; Celi, A. et al. *Proc Natl Acad Sci USA* (1994) 91:8767-8771).

SUMMARY OF THE INVENTION

The present invention provides methods and compositions for the regulation of hemostatic and thrombotic processes using modulators of P-selectin activity (e.g., inducers and inhibitors of P-selectin activity), as well as for the diagnosis and treatment of hemostatic disorders.

In one aspect, the invention provides methods for inducing hemostasis in a subject, comprising administering an inducer of P-selectin activity to the subject. In one embodiment, the inducer of P-selectin activity increases the level of circulating soluble P-selectin in the subject. The inducer of P-selectin activity may increase the level of soluble P-selectin polypeptide by increasing the proteolytic cleavage of P-selectin from the cell surface, or by increasing P-selectin gene expression. In another embodiment, the inducer of P-selectin activity binds to a P-selectin ligand or receptor (e.g., PSGL-1) and mimics the activity of a P-selectin polypeptide, e.g., a soluble P-selectin polypeptide.

In an exemplary embodiment, the invention provides methods for inducing hemostasis in a subject, comprising administering soluble P-selectin polypeptide to the subject. In another embodiment, an isolated nucleic acid molecule comprising a nucleotide sequence which encodes a soluble P-selectin polypeptide is administered to the subject to induce hemostasis. In a further embodiment, hemostasis is induced in a subject by administering a recombinant cell expressing soluble P-selectin polypeptide.

In another aspect, the invention provides methods for treating or preventing a disorder associated with hypocoagulation, e.g., a hemorrhagic disorder, in a subject, comprising administering to the subject an inducer of P-selectin activity. In one embodiment, a soluble P-selectin polypeptide is administered to a subject to treat or prevent a disorder associated with hypocoagulation.

In a further aspect, the invention provides methods for treating a vasculature-associated disease in a subject, comprising administering to the subject an inducer of P-selectin activity. In a preferred embodiment, a soluble P-selectin polypeptide is administered to a subject to treat or prevent a vasculature-associated disease. In one embodiment, the vasculature-associated disease is a tumor. In another embodiment, the subject is further treated with a molecule effective to induce a procoagulant state in tumor associated vasculature, e.g., a molecule comprising a first binding region that binds to a component of a tumor cell or tumor associated vasculature operatively linked to a coagulation factor or a second binding region that binds to a coagulation factor.

Another aspect of the invention provides methods for reducing hemostasis in a subject, comprising administering to the subject an inhibitor of P-selectin activity. In one embodiment, the inhibitor of P-selectin activity decreases the level of soluble P-selectin in plasma of the subject. The inhibitor of P-selectin activity may decrease the level of the soluble P-selectin polypeptide by decreasing the proteolytic cleavage of P-selectin from the cell surface, or decreasing P-selectin gene expression. In another embodiment, the inhibitor of P-selectin activity is an anti-P-selectin antibody. In yet another embodiment, the inhibitor of P-selectin activity is a recombinant soluble PSGL-1 polypeptide. In a further embodiment, the invention provides a method for reducing hemostasis in a subject, comprising administering an isolated nucleic acid molecule comprising a nucleotide sequence which is antisense to a nucleotide sequence which encodes a P-selectin polypeptide, e.g., a soluble P-selectin polypeptide.

In another aspect, the invention provides methods for treating or preventing a thrombotic disorder in a subject, comprising administering to the subject an inhibitor of P-selectin activity. Thrombotic disorders that may be treated or prevented using the methods of the invention include arteriosclerosis, deep vein thrombosis, angina, e.g., unstable angina, and restenosis following medical intervention.

In a further aspect, the invention provides methods for modulating hemostatic potential in a subject, comprising modulating P-selectin activity in the subject. In one embodiment, a modulator (e.g., an inducer or inhibitor) of P-selectin activity is administered to a subject to modulate hemostatic potential. A modulator of soluble P-selectin activity may act by regulating the level of soluble P-selectin in the plasma of the subject.

Another aspect of the invention provides a method for diagnosing a procoagulant state in a subject, comprising determining an increased level of P-selectin activity in a biological sample of the subject. In one embodiment, the level of soluble P-selectin in a test sample of blood or plasma from a subject is compared to the level of soluble P-selectin in a control blood or plasma sample from a subject with normal hemostatic activity, wherein an increased level of soluble P-selectin in the test sample as compared to the control sample is an indication of a procoagulant state in the subject.

In another aspect, the invention provides a method for identifying a subject having a thrombotic disorder, or at risk for developing a thrombotic disorder, comprising determining an increased P-selectin activity in a biological sample of the subject. In one embodiment, a sample of blood or plasma obtained from a subject is contacted with a P-selectin binding substance, and the detection of increased levels of soluble P-selectin polypeptide in the sample identifies a subject having a thrombotic disorder, or at risk for developing a thrombotic disorder.

Another aspect of the invention provides a method for identifying a compound capable of modulating hemostasis, comprising assaying the ability of the test compound to modulate a P-selectin activity. In one embodiment, the P-selectin activity is the expression of soluble P-selectin.

In a further aspect, the invention provides compositions for modulating hemostasis comprising at least one modulator of P-selectin activity.

Other features and advantages of the invention will be apparent from the following detailed description and claims.

BRIEF DESCRIPTION OF THE DRAWINGS

FIG. 2 shows fibrin formation in a perfusion chamber of non-anticoagulated blood from wild type mice (WT), P-selectin deficient mice (P-sel–/–), and ΔCT mice.

FIG. 3 shows macroscopic and microscopic grading of hemorrhagic lesions formed in a local Shwartzman reaction in wild type mice (WT) that were either untreated, perfused with human IgG1, or perfused with soluble P-selectin-Ig (s-P-sel), and ΔCT mice.

FIG. 7 shows the number of microparticles expressing tissue factor in wild type (WT) and ΔCT mice.

FIG. 9 shows the prothrombin clotting time of wild type mice (WT), and von Willebrand factor deficient mice (vWF–/–) that were either untreated, perfused with human IgG1, or perfused with soluble P-selectin-Ig (sPselIg).

FIG. 10 shows the bleeding time in hemophilia A mice treated with either human IgG1 or soluble P-selectin-Ig (P-sel-Ig).

DETAILED DESCRIPTION OF THE INVENTION

Figure 1:
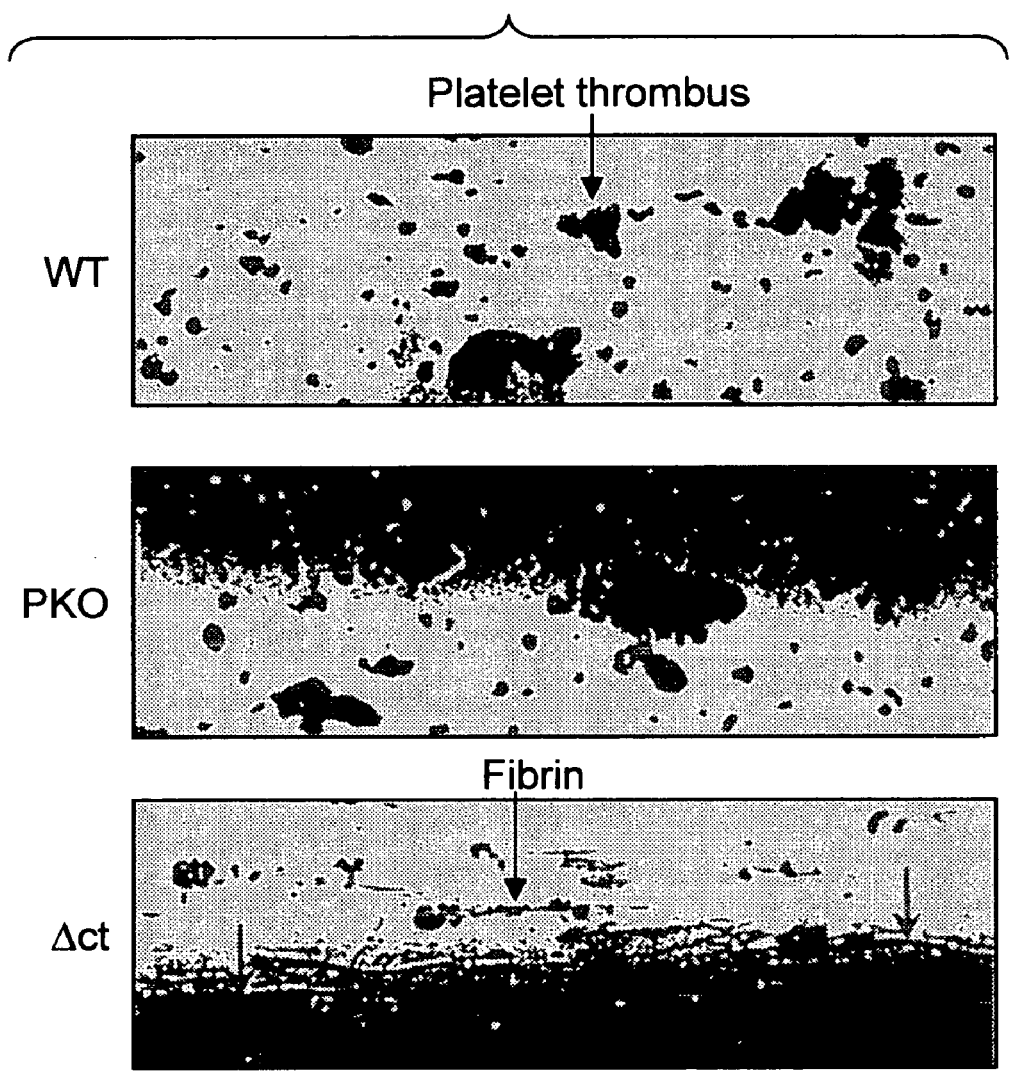
FIG. 1 is a photograph of en face examination of the thrombotic deposits in wild-type mice (WT), P-selectin deficient mice (PKO), and ΔCT mice formed after a 2 minute non-anticoagulated blood perfusion (blood flow, left to right). The white arrow indicates platelet rich thrombus; the black arrow indicates fibrin tail formed distally to the platelet thrombus.

The present invention provides modulators (e.g., inducers, inhibitors) of P-selectin activity as therapeutic and diagnostic agents for the regulation of hemostasis. The present invention is based on the discovery that soluble P-selectin induces a procoagulant state in a mammal, for example a mouse or a human, (e.g., by increasing the numbers of microparticles containing tissue factor in the blood, reducing bleeding time, and/or reducing clotting time).

As used herein, the term "modulator of P-selectin activity" includes a compound or agent that is capable of modulating or regulating at least one P-selectin activity, as described herein. In a preferred embodiment, a modulator of P-selectin activity modulates the expression of soluble P-selectin. A modulator of P-selectin activity can be an inducer of P-selectin activity or an inhibitor of P-selectin activity. As used herein, an "inducer of P-selectin activity" stimulates, enhances, and/or mimics a P-selectin activity. As used herein, an "inhibitor of P-selectin activity" reduces, blocks or antagonizes a P-selectin activity.

As used interchangeably herein, a "P-selectin activity", "biological activity of P-selectin" or "functional activity of P-selectin" refers to an activity exerted by a P-selectin polypeptide or nucleic acid molecule on a P-selectin responsive cell (e.g., a hematopoietic cell or lymphocyte) or tissue, or on a P-selectin ligand or receptor, as determined in vitro and in vivo, according to standard techniques. In an exemplary embodiment, a P-selectin activity is the ability to modulate hemostasis. In one embodiment, a P-selectin activity is a procoagulant activity. In another embodiment, a P-selectin activity is the ability to increase the number of microparticles containing tissue factor. In yet another embodiment, a P-selectin activity is the ability to bind a P-selectin ligand, e.g., PSGL-1.

Accordingly, the invention provides a method for regulating hemostasis in a subject, at least in part, by increasing or decreasing P-selectin activity in the subject (e.g., by increasing or decreasing levels of circulating soluble P-selectin). As used interchangeably herein, the terms "hemostasis", "hemostatic activity", or "hemostatic potential" refer to the control of bleeding, including the physiological properties of vasoconstriction and coagulation. Blood coagulation assists in maintaining the integrity of mammalian circulation after injury, inflammation, disease, congenital defect, dysfunction or other disruption. After initiation of clotting, blood coagulation proceeds through the sequential activation of certain plasma proenzymes to their enzyme forms (see, for example, Coleman, R. W. et al. (eds.) *Hemostasis and Thrombosis, Second Edition*, (1987)). These plasma glycoproteins, including Factor XII, Factor XI, Factor IX, Factor X, Factor VII, and prothrombin, are zymogens of serine proteases. Most of these blood clotting enzymes are effective on a physiological scale only when assembled in complexes on membrane surfaces with protein cofactors such as Factor VIII and Factor V. Other blood factors modulate and localize clot formation, or dissolve blood clots. Activated protein C is a specific enzyme that inactivates procoagulant components. Calcium ions are involved in many of the component reactions. Blood coagulation follows either the intrinsic pathway, where all of the protein components are present in blood, or the extrinsic pathway, where the cell-membrane protein tissue factor plays a critical role. Clot formation occurs when fibrinogen is cleaved by thrombin to form fibrin. Blood clots are composed of activated platelets and fibrin.

As used herein, the term "procoagulant state" includes physiological conditions that are conducive to and/or promote blood clotting, hemostasis, and/or thrombosis. Hemostatic potential, e.g., the potential for blood coagulation under the appropriate physiological conditions, or hemostatic activity can be assessed using well established laboratory tests including prothrombin time (PT), activated partial thromboplastin time (APTT), bleeding time, and thrombin time. As used interchangeably herein, "modulating or modulation of hemostasis" and "regulating or regulation of hemostasis" includes the induction (e.g., stimulation, increase) of hemostasis, as well as the inhibition (e.g., reduction, decrease) of hemostasis.

In one aspect of the invention, hemostasis is induced in a subject by administering an inducer of P-selectin activity. In an exemplary embodiment, an inducer of P-selectin activity increases the plasma level of soluble P-selectin polypeptide. In this respect, an inducer of P-selectin activity may act to stimulate the translocation of P-selectin from a cellular storage pool to the cell surface, or to increase the proteolytic cleavage and release of soluble P-selectin from the surface of a cell expressing P-selectin, e.g., an endothelial cell or a platelet. In another embodiment, an inducer of P-selectin activity increases P-selectin gene expression by stimulating either gene transcription or translation. In a preferred embodiment, an inducer of P-selectin activity will preferentially stimulate the expression of an alternatively spliced isoform of the P-selectin gene encoding a soluble P-selectin polypeptide lacking the transmembrane domain. In yet another embodiment, an inducer of P-selectin activity binds to a P-selectin ligand or receptor (e.g., PSGL-1) and mimics the activity of a P-selectin polypeptide on a P-selectin responsive cell. The inducer of P-selectin activity can thereby elicit a biological response of P-selectin, e.g., the release of microparticles containing tissue factor. Accordingly, in one embodiment, an inducer of P-selectin activity is an antibody, e.g., an anti-PSGL-1 antibody.

In another embodiment of the invention, a soluble P-selectin polypeptide is administered to a subject to induce hemostasis. As used herein, a "soluble P-selectin polypeptide" includes a P-selectin polypeptide comprising amino acid sequences corresponding to the extracellular domain of a P-selectin protein, or a fragment thereof. The nucleic acid and amino acid sequences of P-selectin proteins have been described (see, for example, Sanders, W. E. et al. (1992) *Blood* 80:795-800; and GenBank Accession Numbers NM_003005 and M25322 (human); GenBank Accession Numbers NM_013114 and L23088 (rat); GenBank Accession Numbers NM_011347 and M87861 (mouse); and GenBank Accession Number L12041 (bovine)). In another embodiment, a soluble P-selectin polypeptide comprises at least a lectin domain, an EGF-like repeat, and at least two complement-binding domains of a P-selectin protein. In yet another embodiment, a soluble P-selectin polypeptide binds to a P-selectin ligand, e.g., PSGL-1. In a preferred embodiment, a soluble P-selectin polypeptide of the invention is a soluble P-selectin fusion protein. In one embodiment, the P-selectin fusion protein is a P-selectin-Ig fusion protein comprising a signal sequence, a lectin domain, an EGF-like repeat, and at least two complement-binding domains of a P-selectin protein operatively linked to the Fc region (hinge, C1 and C2) of an immunoglobulin, e.g., human IgG1.

In a further embodiment of the invention, hemostasis is induced in a subject by administering an isolated nucleic acid molecule comprising a nucleotide sequence which encodes a soluble P-selectin polypeptide. In yet another embodiment, a recombinant cell expressing a soluble P-selectin polypeptide is administered to a subject to induce hemostasis.

Another embodiment of the invention provides methods for inducing hemostasis in a subject presenting insufficient hemostatic function, such as a subject having, or at risk of developing a disorder associated with hypocoagulation. As used herein, the term "hypocoagulation" refers to a decreased ability or inability to form blood clots. Such disorders include hemorrhagic disorders, e.g., hemophilia (e.g., hemophilia A or B), and disorders resulting from a deficiency in clotting factors or platelet ligands, e.g., a deficiency in von Willebrand's factor resulting in von Willebrand disease. The induction of a procoagulant state would prevent or stop spontaneous bleeding and would also be beneficial preceding surgical intervention in a patient, or to promote wound healing.

The methods of the present invention are also useful for the treatment of a vasculature-associated disease. As used herein, a "vasculature-associated disease" is a disease having a pathology that is dependent on a vascular blood supply. Thus, it is contemplated that achieving coagulation in the vasculature of the disease site, e.g., in the intratumoral vasculature of a solid tumor, would prove beneficial. Such vasculature-associated diseases include benign and malignant tumors or growths, such as BPH, diabetic retinopathy, vascular restenosis, arteriovenous malformations (AVM), meningioma, hemangioma, neovascular glaucoma and psoriasis. Also included within this group are synovitis, dermatitis, endometriosis, angiofibroma, rheumatoid arthritis, atherosclerotic plaques, corneal graft neovascularization, hemophilic joints, hypertrophic scars, osler-weber syndrome, pyogenic granuloma retrolental fibroplasia, scleroderma, trachoma, and vascular adhesions.

In one embodiment, an inducer of P-selectin activity, e.g., soluble P-selectin, is administered in addition to therapies designed to induce thrombosis of tumor blood vessels, in order to potentiate tumor necrosis. Such therapies utilize strategies for targeting coagulation factors to the tumor vasculature, for example, as described in U.S. Pat. No. 5,877,289. Markers of tumor vasculature or stroma may be specifically induced and then targeted using a binding ligand, such as an antibody. Exemplary inducible antigens include E-selectin, P-selectin, MHC Class II antigens, VCAM-1, ICAM-1, endoglin, ligands reactive with LAM-1, vascular addressins and other adhesion molecules.

Moreover, the present invention provides a method for reducing hemostasis in a subject by administering an inhibitor of P-selectin activity. The inhibition of hemostasis, e.g., clot formation, is desirable in situations where vessel patency is of importance.

In an exemplary embodiment, an inhibitor of P-selectin activity decreases the level of circulating soluble P-selectin in the subject. The inhibitor of P-selectin activity may act to decrease the translocation of P-selectin from a cellular storage pool to the cell surface, or to decrease the proteolytic cleavage and release of soluble P-selectin from the surface of a cell expressing P-selectin, e.g., an endothelial cell or a platelet. In another embodiment, an inhibitor of P-selectin activity decreases P-selectin gene expression by reducing either gene transcription or translation. In a preferred embodiment, an inhibitor of P-selectin activity will preferentially reduce the expression of an alternatively spliced isoform of the P-selectin gene encoding a soluble P-selectin polypeptide lacking the transmembrane domain. In yet another embodiment, an inhibitor of P-selectin activity acts as an antagonist, wherein it binds to a P-selectin ligand or receptor (e.g., PSGL-1) and blocks the activity of a P-selectin polypeptide on a P-selectin responsive cell. In one embodiment of the invention, an inhibitor of P-selectin activity is an anti-P-selectin antibody. In another embodiment, an inhibitor of P-selectin activity is a soluble PSGL-1 polypeptide. PSGL-1 nucleic acids, polypeptides, and soluble forms thereof are disclosed in U.S. Pat. No. 5,843,707.

Alternatively, the invention provides a method for reducing hemostasis in a subject by administering an isolated nucleic acid molecule comprising a nucleotide sequence which is antisense, e.g., complementary to, to a nucleotide sequence encoding a P-selectin polypeptide.

Thus, the methods of the invention are useful for the treatment or prevention of thrombotic disorders. As used herein, the term "thrombotic disorder" includes any disorder or condition characterized by excessive or unwanted coagulation or hemostatic activity, or a hypercoagulable state. Thrombotic disorders include disorders diseases involving platelet adhesion and thrombus formation, and may manifest as an increased propensity to form thromboses, e.g., an increased number of thromboses, thrombosis at an early age, a familial tendency towards thrombosis, and thrombosis at unusual sites. Examples of thrombotic disorders include, but are not limited to, thromboembolism, deep vein thrombosis, pulmonary embolism, stroke, myocardial infarction, miscarriage, thrombophilia associated with anti-thrombin III deficiency, protein C deficiency, protein S deficiency, resistance to activated protein C, dysfibrinogenemia, fibrinolytic disorders, homocystinuria, pregnancy, inflammatory disorders, myeloproliferative disorders, arteriosclerosis, angina, e.g., unstable angina, disseminated intravascular coagulation, thrombotic thrombocytopenic purpura, cancer metastasis, sickle cell disease, and glomerular nephritis. In addition, inhibitors of soluble P-selectin expression or activity are administered to prevent thrombotic events or to prevent re-occlusion during or after therapeutic clot lysis or procedures such as angioplasty or surgery.

Furthermore, measuring the level P-selectin activity in a biological sample, e.g., in blood, would provide diagnostic information of a procoagulant state, e.g., the likelihood of a thrombotic or clotting event. Accordingly, in one embodiment, the invention provides a method for diagnosing a procoagulant state in a subject by detecting an increased level of circulating soluble P-selectin as compared with the levels of soluble P-selectin in the blood of individual with clinically established normal levels of hemostatic activity. In another embodiment, the invention provides a method of identifying a subject having a thrombotic disorder, or at risk for developing a thrombotic disorder, by detecting the presence of increased levels of P-selectin activity (e.g., increased levels of circulating soluble P-selectin).

As used herein, a "hemostatic disorder" includes a disorder or condition characterized by aberrant or unwanted hemostatic activity. A hemostatic disorder may result from excessive coagulant activity, e.g., a thrombotic disorder, or it may result from insufficient coagulant activity, e.g., a hemorrhagic disorder.

Furthermore, another aspect of the invention provides a method for identifying a compound capable of modulating hemostasis by assaying the ability of the compound to modulate a P-selectin activity, e.g., the expression of soluble P-selectin.

Various aspects of the invention are described in further detail in the following subsections.

I. Isolated P-Selectin Proteins and Anti-P-Selectin Antibodies

The methods of the invention include the use of isolated P-selectin polypeptides, and biologically active portions thereof. As used herein, a "P-selectin protein" or "P-selectin polypeptide" includes a soluble P-selectin polypeptide and a soluble P-selectin fusion protein.

The genomic organization and coding sequence for human P-selectin have been determined, and the cDNA has been cloned and sequenced (see, for example, GenBank Accession Numbers NM_003005 and M25322). In addition, the sequences encoding rat (GenBank Accession Numbers NM_013114 and L23088), mouse (GenBank Accession Numbers NM_011347 and M87861), and bovine (GenBank Accession Number L12041) P-selectin have been disclosed. Furthermore, a comparison of the amino acid sequences and structural domains of human and mouse P-selectin is disclosed in Sanders, W E et al. (1992) Blood 80:795-800.

Isolated soluble P-selectin proteins for use in the methods of the present invention preferably have an amino acid sequence that is sufficiently identical to the amino acid sequence of a native P-selectin protein. As used herein, the term "sufficiently identical" refers to an amino acid (or nucleotide) sequence which contains a sufficient or minimum number of identical or equivalent (e.g., an amino acid residue that has a similar side chain) amino acid residues (or nucleotides) to a P-selectin amino acid (or nucleotide) sequence such that the polypeptide shares common structural domains or motifs, and/or a common functional activity with a native P-selectin protein. For example, amino acid or nucleotide sequences which share common structural domains have at least 30%, 40%, or 50% identity, preferably 60% identity, more preferably 70%-80%, and even more preferably 90-95% identity across the amino acid sequences of the domains and contain at least one, and more preferably two or more structural domains or motifs, are defined herein as sufficiently identical. For example, a soluble P-selectin polypeptide may comprise at least one or more of the following domains: a signal peptide, a lectin domain, an EGF-like repeat, a complement binding domain, and a cytoplasmic domain. Furthermore, amino acid or nucleotide sequences which share at least 30%, 40%, or 50%, preferably 60%, more preferably 70-80%, or 90-95% identity and share a common functional activity (e.g., a soluble P-selectin activity as described herein) are defined herein as sufficiently identical. A P-selectin polypeptide may differ in amino acid sequence from the P-selectin polypeptides disclosed herein due to natural allelic variation or mutagenesis. Accordingly, isolated soluble P-selectin polypeptides having a P-selectin activity can be used in the methods of the invention.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48): 444453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.,* 4:11-17 (1988)) which has been incorporated into the ALIGN program (version 2.0), using a PAM120 weight residue table, a gap length penalty of 12 and a gap penalty of 4.

As used herein, a "biologically active portion" of a P-selectin polypeptide (e.g., a soluble P-selectin polypeptide) includes a fragment of a P-selectin polypeptide which retains a P-selectin polypeptide activity. Typically, a biologically active portion of a P-selectin polypeptide comprises at least one domain or motif with at least one activity of the P-selectin polypeptide, e.g., modulating hemostatic activity. Biologically active portions of a P-selectin polypeptide include polypeptides comprising amino acid sequences sufficiently identical to or derived from the amino acid sequence of a P-selectin protein, which include less amino acids than the full length P-selectin polypeptide, and exhibit at least one activity of a soluble P-selectin polypeptide. Biologically active portions of a P-selectin polypeptide can be used as targets for developing agents which modulate a P-selectin polypeptide activity, e.g., a hemostatic activity. A biologically active portion of a P-selectin polypeptide comprises a polypeptide which can be prepared by recombinant techniques and evaluated for one or more of the functional activities of a P-selectin polypeptide.

In one embodiment, P-selectin polypeptides can be isolated from cells or tissue sources by an appropriate purification scheme using standard protein purification techniques. For example, a soluble P-selectin polypeptide can be isolated from the culture medium of cells, e.g., activated endothelial cells, that have been induced to shed P-selectin from the cell surface. In another embodiment, P-selectin polypeptides are produced by recombinant DNA techniques. For example, a soluble P-selectin polypeptide can be isolated from a host cell transfected with a polynucleotide sequence encoding a soluble isoform of P-selectin (e.g., an isoform of P-selectin lacking a transmembrane domain) or a soluble P-selectin fusion protein. Alternative to recombinant expression, a soluble P-selectin polypeptide can be synthesized chemically using standard peptide synthesis techniques.

An "isolated" or "purified" polypeptide or protein, or biologically active portion thereof is substantially free of cellular material or other contaminating proteins from the cell or tissue source from which the P-selectin polypeptide is derived, or substantially free from chemical precursors or other chemicals when chemically synthesized. The language "substantially free of cellular material" includes preparations of P-selectin polypeptide in which the protein is separated from cellular components of the cells from which it is isolated or recombinantly produced. In one embodiment, the language "substantially free of cellular material" includes preparations of P-selectin protein having less than about 30% (by dry weight) of non-P-selectin protein (also referred to herein as a "contaminating protein"), more preferably less than about 20% of non-P-selectin protein, still more preferably less than about 10% of non-P-selectin protein, and most preferably less than about 5% non-P-selectin protein. When the P-selectin polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of P-selectin polypeptide in which the protein is separated from chemical precursors or other chemicals which are involved in the synthesis of the protein. In one embodiment, the language "substantially free of chemical precursors or other chemicals" includes preparations of P-selectin polypeptide having less than about 30% (by dry weight) of chemical precursors or non-P-selectin chemicals, more preferably less than about 20% chemical precursors or non-P-selectin chemicals, still more preferably less than about 10% chemical precursors or non-P-selectin chemicals, and most preferably less than about 5% chemical precursors or non-P-selectin chemicals.

The methods of the invention may also use soluble P-selectin polypeptides that are chimeric or fusion proteins. As used herein, a soluble P-selectin "chimeric protein" or "fusion protein" comprises a soluble P-selectin polypeptide operatively linked to a non-soluble P-selectin polypeptide. A "soluble P-selectin polypeptide" includes a P-selectin polypeptide that comprises amino acid sequences corresponding to the extracellular domain of a P-selectin protein, or a biologically active portion thereof, whereas a "non-soluble P-selectin polypeptide" refers to a polypeptide having an amino acid sequence corresponding to a protein which is not substantially homologous to a P-selectin polypeptide, e.g., a protein which is different from the soluble P-selectin polypeptide and which is derived from the same or a different organism. Within a soluble P-selectin fusion protein the soluble P-selectin polypeptide may include, for example, all or a portion of the extracellular domain of a P-selectin protein. In a preferred embodiment, a soluble P-selectin fusion protein comprises at least a signal sequence, a lectin domain, an EGF-like repeat, and at least two complement-binding domains of a P-selectin protein. Within the fusion protein, the term "operatively linked" is intended to indicate that the soluble P-selectin polypeptide and the non-soluble P-selectin polypeptide are fused in-frame to each other. The non-soluble P-selectin polypeptide can be fused to the N-terminus or C-terminus of the soluble P-selectin polypeptide.

For example, in a preferred embodiment, the fusion protein is a soluble P-selectin-immunoglobulin fusion protein in which the Fc region, e.g., the hinge, C1 and C2 sequences, of an immunoglobulin, (e.g., human IgG1) is fused to the C-terminus of the soluble P-selectin sequences. Selectin immunoglobulin chimeras can be constructed essentially as described in WO 91/08298. Such fusion proteins can facilitate the purification of recombinant soluble P-selectin polypeptides. In another embodiment, the fusion protein is a soluble P-selectin polypeptide containing a heterologous signal sequence at its N-terminus. In certain host cells (e.g., mammalian host cells), expression and/or secretion of soluble P-selectin can be increased through use of a heterologous signal sequence.

The soluble P-selectin polypeptides and fusion proteins of the invention can be incorporated into pharmaceutical compositions and administered to a subject in vivo. In an exemplary embodiment, a soluble P-selectin polypeptide or fusion protein may be used to modulate hemostasis in a subject (e.g., induce a procoagulant state). In another embodiment, a soluble P-selectin polypeptide or fusion protein may be used to treat a hemostatic disorder, e.g., a hemorrhagic disorder. In another embodiment, a soluble P-selectin polypeptide or fusion protein may be used to treat a vasculature-associated disease. Use of soluble P-selectin polypeptides and fusion proteins may also be useful therapeutically for the treatment of disorders caused by, for example, (i) aberrant modification or mutation of a gene encoding a P-selectin protein; (ii) misregulation of a P-selectin gene; and (iii) aberrant post-translational modification of a P-selectin protein. In addition, the soluble P-selectin polypeptides and fusion proteins can be used to affect the bioavailability of a P-selectin ligand, e.g., PSGL-1.

Moreover, the soluble P-selectin polypeptides and fusion proteins of the invention can be used as immunogens to produce anti-P-selectin antibodies in a subject, to purify P-selectin ligands, and in screening assays to identify molecules which modulate P-selectin activity, and/or modulate the interaction of a P-selectin polypeptide with a P-selectin ligand or receptor.

Preferably, a soluble P-selectin fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A soluble P-selectin-encoding nucleic acid can be cloned into such an expression vector such that the fusion moiety is linked in-frame to the soluble P-selectin polypeptide.

The methods of the present invention may also include the use of variants of a P-selectin polypeptide which function as either P-selectin agonists (mimetics) or as P-selectin antagonists. Variants of the P-selectin polypeptide can be generated by mutagenesis, e.g., discrete point mutation or truncation of a P-selectin protein. An agonist of a P-selectin polypeptide can retain substantially the same, or a subset, of the biological activities of the naturally occurring form of a P-selectin polypeptide. An antagonist of a P-selectin polypeptide can inhibit one or more of the activities of a native form of the P-selectin polypeptide by, for example, competitively modulating a P-selectin selectin activity (e.g., a hemostatic activity) of a P-selectin polypeptide. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the P-selectin polypeptide.

In one embodiment, variants of a soluble P-selectin polypeptide which function as either soluble P-selectin agonists (mimetics) or as soluble P-selectin antagonists can be identified by screening mutants, e.g., truncation mutants, of a soluble P-selectin polypeptide for soluble P-selectin polypeptide agonist or antagonist activity. The activity of a variant soluble P-selectin polypeptide, e.g., the ability to modulate hemostatic activity, can be assessed in an animal model such as the animal models described and exemplified herein, e.g., a P-selectin deficient mouse, or a von Willebrand factor deficient mouse.

An isolated P-selectin polypeptide, or a portion or fragment thereof, can be used as an immunogen to generate antibodies that bind P-selectin using standard techniques for polyclonal and monoclonal antibody preparation (see, generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.* 3:231-36). Moreover, the ordinarily skilled artisan will appreciate that there are many variations of such methods which also would be useful.

Alternative to preparing monoclonal antibody-secreting hybridomas, a monoclonal anti-P-selectin antibody can be identified and isolated by screening a recombinant combinatorial immunoglobulin library (e.g., an antibody phage display library) with P-selectin to thereby isolate immunoglobulin library members that bind P-selectin. Kits for generating and screening phage display libraries are commercially available (e.g., the Pharmacia *Recombinant Phage Antibody System*, Catalog No. 27-9400-01; and the Stratagene *SufZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrad et al. (1991) *Bio/Technology* 9:1373-1377; Hoogenboom et al. (1991) *Nuc. Acid Res.* 19:4133-4137; Barbas et al. (1991) *Proc. Natl. Acad. Sci. USA* 88:7978-7982; and McCafferty et al. *Nature* (1990) 348:552-554.

Additionally, recombinant anti-P-selectin antibodies, such as chimeric and humanized monoclonal antibodies, comprising both human and non-human portions, which can be made using standard recombinant DNA techniques, can also be used in the methods of the present invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-P-selectin antibody (e.g., a monoclonal antibody) can be used in the methods of the invention to modulate the expression and/or activity of a soluble P-selectin polypeptide. Alternatively, an antibody against a P-selectin ligand or receptor, e.g., PSGL-1, may be useful in the methods of the invention. For example, an anti-PSGL-1 antibody may be used to mimic the activity of soluble P-selectin. In one embodiment an activating anti-PSGL-1 antibody induces the release of microparticles containing tissue factor.

An anti-P-selectin antibody can also be used to isolate soluble P-selectin polypeptides or fusion proteins by standard techniques, such as affinity chromatography or imunoprecipitation. An anti-P-selectin antibody can facilitate the purification of natural soluble P-selectin from cell cultures and of recombinantly produced soluble P-selectin expressed in host cells. Moreover, an anti-P-selectin antibody can be used to detect soluble P-selectin polypeptide (e.g., in a blood sample) in order to evaluate the abundance and pattern of expression of the soluble P-selectin polypeptide. Anti-P-selectin antibodies can be used diagnostically to monitor protein levels in blood as part of a clinical testing procedure, e.g., to, for example, determine hemostatic activity, i.e., a procoagulant state. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

II. Isolated Nucleic Acid Molecules

The methods of the invention include the use of isolated nucleic acid molecules that encode P-selectin polypeptides (e.g., a soluble P-selectin polypeptide) or biologically active portions thereof. The nucleotide sequences encoding human (GenBank Accession Numbers NM_003005 and M25322), rat (GenBank Accession Numbers NM_013114 and L23088), mouse (GenBank Accession Numbers NM_011347 and M87861), and bovine (GenBank Accession Number L12041) P-selectin have been disclosed.

As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule encoding soluble P-selectin can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule encoding soluble P-selectin, a soluble P-selectin fusion protein, or a portion thereof, can be isolated using standard molecular biology techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to P-selectin nucleotide sequences can be prepared by standard synthetic techniques, e.g., using an automated DNA synthesizer.

A nucleic acid fragment encoding a "biologically active portion" of a P-selectin polypeptide can be prepared by isolating a portion of the nucleotide sequence of a P-selectin gene having a P-selectin biological activity (the biological activities, e.g., the hemostatic activity, of soluble P-selectin are described herein), expressing the encoded portion of the P-selectin polypeptide (e.g., by recombinant expression in vitro) and assessing the activity of the encoded portion of the P-selectin polypeptide.

The skilled artisan will further appreciate that changes can be introduced by mutation into the nucleotide sequence encoding a P-selectin polypeptide, thereby leading to changes in the amino acid sequence of the encoded P-selectin polypeptide, without altering the functional ability of the P-selectin polypeptide. For example, nucleotide substitutions leading to amino acid substitutions at "non-essential" amino acid residues can be made in the sequence of a P-selectin gene. A "non-essential" amino acid residue is a residue that can be altered from the wild-type sequence of a P-selectin polypeptide without altering the biological activity, whereas an "essential" amino acid residue is required for biological activity. For example, amino acid residues that are conserved among the P-selectin proteins from different species are predicted to be particularly unamenable to alteration.

Accordingly, the methods of the invention may include the use of nucleic acid molecules encoding P-selectin polypeptides that contain changes in amino acid residues that are not essential for activity.

An isolated nucleic acid molecule encoding a P-selectin polypeptide can be created by introducing one or more nucleotide substitutions, additions or deletions into the nucleotide sequence of a P-selectin gene such that one or more amino acid substitutions, additions or deletions are introduced into the encoded protein. Mutations can be introduced into a nucleic acid sequence by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine., phenylalanine, tryptophan, histidine). Thus, a predicted nonessential amino acid residue in a soluble P-selectin polypeptide is preferably replaced with another amino acid residue from the same side chain family. Alternatively, in another embodiment, mutations can be introduced randomly along all or part of a P-selectin coding sequence, such as by saturation mutagenesis, and the resultant mutants can be expressed recombinantly and screened for biological activity to identify mutants that retain activity, e.g., in an animal model described herein. In a preferred embodiment, a mutant soluble P-selectin polypeptide protein can be assayed for the ability to modulate hemostatic activity.

In addition to the nucleic acid molecules encoding P-selectin polypeptides described herein, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire P-selectin coding strand, or to only a portion thereof. In one embodiment, an antisense nucleic acid molecule is antisense to a "coding region" of the coding strand of a nucleotide sequence encoding P-selectin. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding P-selectin. The term "noncoding region" refers to 5' and 3' sequences which flank the coding region that are not translated into amino acids.

Given the coding strand sequences encoding P-selectin, antisense nucleic acids of the invention can be designed according to the rules of Watson and Crick base pairing. The antisense nucleic acid molecule can be complementary to the entire coding region of P-selectin mRNA, but more preferably is an oligonucleotide which is antisense to only a portion of the coding or noncoding region of P-selectin mRNA. For example, the antisense oligonucleotide can be complementary to the region surrounding the translation start site of P-selectin mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

In yet another embodiment, the P-selectin nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'eefe et al. Proc. Natl. Acad. Sci. 93: 14670-675.

PNAs of P-selectin nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of P-selectin nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of P-selectin can be modified, (e.g., to enhance their stability or cellular uptake), by attaching lipophilic or other helper groups to PNAs, by the formation of PNA-DNA chimeras, or by the use of liposomes or other techniques of drug delivery known in the art. For example, PNA-DNA chimeras of P-selectin nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996)supra). The synthesis of PNA-DNA chimeras can be performed as described in Hyrup B. (1996) supra and Finn P. J. et al. (1996) *Nucleic Acids Res.* 24 (17): 3357-63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al. (1989) *Nucleic Acid Res.* 17: 5973-88). PNA monomers are then coupled in a stepwise manner to produce a chimeric molecule with a 5' PNA segment and a 3' DNA segment (Finn P. J. et al. (1996)supra). Alternatively, chimeric molecules can be synthesized with a 5' DNA segment and a 3' PNA segment (Peterser, K. H. et al. (1975) *Bioorganic Med. Chem. Lett.* 5: 1119-11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. W088/09810) or the blood-brain barrier (see, e.g., PCT Publication No. W089/10134). In addition, oligonucleotides can be modified with hybridization-triggered cleavage agents (See, e.g., Krol et al. (1988) *Bio-Techniques* 6:958-976) or intercalating agents. (See, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

III. Recombinant Expression Vectors and Host Cells

The methods of the invention include the use of vectors, preferably expression vectors, containing a nucleic acid encoding a P-selectin polypeptide (or a portion thereof, e.g., a soluble P-selectin polypeptide). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the methods of the invention may include other forms of expression vectors, such as viral vectors (e.g., replication defective retroviruses, adenoviruses and adeno-associated viruses), which serve equivalent functions.

The recombinant expression vectors used in the methods of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appeciated by those skilled in the art that the design of the expression vector can depend on such factors as the choice of the host cell to be transformed, the level of expression of protein desired, and the like. The expression vectors used in the methods of the invention can be introduced into host cells to thereby produce proteins or peptides, including fusion proteins or peptides, encoded by nucleic acids as described herein (e.g., soluble P-selectin polypeptides, fusion proteins, and the like).

The recombinant expression vectors used in the methods of the invention can be designed for expression of P-selectin polypeptides or fusion proteins in prokaryotic or eukaryotic cells, e.g., for use in the methods of the invention. For example, soluble P-selectin polypeptides or fusion proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E.* coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility and/or stability of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, NJ) which fuse glutathione S-transferase (GST), maltose E binding protein, or protein A, respectively, to the target recombinant protein.

Purified P-selectin fusion proteins (e.g., soluble P-selectin-Ig) can be utilized to modulate hemostatic potential, as described and exemplified herein. In one embodiment, a soluble P-selectin fusion protein expressed in a retroviral expression vector of the present invention can be utilized to infect cells, e.g., hematopoietic cells, which are subsequently transplanted into recipients. The hemostatic activity of the subject recipient is then examined after sufficient time has passed (e.g., six (6) weeks).

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

In another embodiment, the P-selectin expression vector is a yeast expression vector. Examples of vectors for expression in yeast *S. cerevisiae* include pYepSec1 (Baldari, et al., (1987) *EMBO J.* 6:229-234), pMFa (Kurjan and Herskowitz, (1982) *Cell* 30:933-943), pJRY88 (Schultz et al., (1987) *Gene* 54:113-123), pYES2 (Invitrogen Corporation, San Diego, Calif.), and picZ (InVitrogen Corp, San Diego, Calif.).

Alternatively, P-selectin polypeptides can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid used in the methods of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector used in the methods of the invention is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989)

*EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), endothelial cell-specific promoters (e.g., KDR/flk promoter; U.S. Pat. No. 5,888,765), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The expression characteristics of an endogenous P-selectin gene within a cell line or microorganism may be modified by inserting a heterologous DNA regulatory element into the genome of a stable cell line or cloned microorganism such that the inserted regulatory element is operatively linked with the endogenous P-selectin gene. For example, an endogenous P-selectin gene which is normally "transcriptionally silent", i.e., a P-selectin gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous P-selectin gene may be activated by insertion of a promiscuous regulatory element that works across cell types.

A heterologous regulatory element may be inserted into a stable cell line or cloned microorganism, such that it is operatively linked with an endogenous P-selectin gene, using techniques, such as targeted homologous recombination, which are well known to those of skill in the art, and described, e.g., in Chappel, U.S. Pat. No. 5,272,071; PCT publication No. WO 91/06667, published May 16, 1991.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to P-selectin mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to use of host cells into which a P-selectin nucleic acid molecule of the invention is introduced, e.g., a P-selectin nucleic acid molecule within a recombinant expression vector or a P-selectin nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a P-selectin polypeptide or fusion protein can be expressed in bacterial cells such as *E. coli*, insect cells, yeast or mammalian cells (such as hematopoietic cells, leukocytes, human umbilical vein endothelial cells (HUVEC), human microvascular endothelial cells (HMVEC), Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a soluble P-selectin polypeptide or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a P-selectin polypeptide or fusion protein for use in the methods of the invention. In one embodiment, a host cell (into which a recombinant expression vector encoding a soluble P-selectin polypeptide or fusion protein has been introduced) is cultured in a suitable medium such that a soluble P-selectin polypeptide or fusion protein is produced. In another embodiment, a soluble P-selectin polypeptide or fusion protein is isolated from the medium or the host cell. A recombinant cell expressing soluble P-selectin or a soluble P-selectin fusion protein can also be administered to a subject to modulate hemostasis.

IV. Methods of Treatment

The present invention discloses methods for modulating hemostatic potential by modulating P-selectin activity (e.g., the levels of soluble P-selectin). Accordingly, the present invention provides for both prophylactic and therapeutic methods of treating a subject at risk of (or susceptible to) or having a hemostatic disorder, e.g., a disorder associated with aberrant or unwanted hemostatic activity, or a vasculature-associated disease. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either soluble P-selectin or modulators of P-selectin activity according to that individual's drug response genotype. Pharmacogenomics allows a clinician or physician to target prophylactic or therapeutic treatments to patients who will most benefit from the treatment and to avoid treatment of patients who will experience toxic drug-related side effects.

A. Prophylactic Methods

The assessment of P-selectin activity can used as a measure of hemostatic activity. Accordingly, in one aspect, the invention provides a method for preventing in a subject, a hemostatic disorder, e.g., a disorder associated with an aberrant or unwanted hemostatic activity, or a vasculature-associated disease by administering to the subject a modulator of P-selectin activity, or a soluble P-selectin polypeptide. Subjects at risk for a hemostatic disorder or a vasculature-associated disease can be identified by, for example, any or a combination of diagnostic or prognostic assays as described herein, e.g., by assessing P-selectin activity in a biological sample (i.e., plasma levels of soluble P-selectin). Administration of a prophylactic agent can occur prior to the manifestation of symptoms characteristic of the hemostatic disorder, such that a disease or disorder is prevented or, alternatively, delayed in its progression. Depending on the type of disorder, for example, a soluble P-selectin polypeptide, or a modulator of P-selectin activity, e.g., a P-selectin agonist or antagonist, can be used for treating the subject. The appropriate agent can be determined based on screening assays described herein.

B. Therapeutic Methods

Described herein are methods and compositions whereby hemostatic disorders, vasculature-associated diseases, and symptoms thereof, may be ameliorated. Certain hemostatic disorders, e.g., a hypocoagulable state or a hemorrhagic disorder, are brought about, at least in part, by the absence or reduction of hemostatic activity. As such, an increase in hemostatic activity would bring about the amelioration of disease symptoms. In addition, certain vasculature-associated diseases are supported by a blood supply to the disease site, for example, to provide oxygen and nutrients. Similarly, the induction of a procoagulant state in the vasculature supplying such disease sites would provide a beneficial effect.

Alternatively, certain other hemostatic diseases, e.g., a thrombotic disorder, are brought about, at least in part, by the presence or increase in hemostatic activity. As such, an reduction in hemostatic activity would bring about the amelioration of disease symptoms.

Techniques for the modulating hemostasis using modulators of P-selectin activity are discussed herein. Accordingly, another aspect of the invention pertains to methods of modulating hemostasis or hemostatic potential for therapeutic purposes.

In an exemplary embodiment, the modulatory methods of the invention involve administering a modulator of P-selectin activity, or a soluble P-selectin polypeptide. A modulator of P-selectin activity includes an agent that modulates (e.g., induces or inhibits) one or more activities of P-selectin, or an agent that modulates soluble P-selectin expression. A modulator of P-selectin activity can be an agent as described herein, such as a nucleic acid or a protein, a naturally-occurring target molecule of a soluble P-selectin polypeptide (e.g., a P-selectin ligand), an anti-P-selectin antibody, a soluble P-selectin agonist or antagonist, a peptidomimetic of a soluble P-selectin agonist or antagonist, or other small molecule. In one embodiment, the agent is an inducer of P-selectin activity. Examples of such inducers include active soluble P-selectin polypeptides, a nucleic acid molecule encoding a soluble P-selectin polypeptide, and a soluble P-selectin mimetic, e.g., an activating anti-PSGL-1 antibody. In another embodiment, the agent is an inhibitor of P-selectin activity. Examples of such inhibitors include antisense soluble P-selectin nucleic acid molecules, anti-P-selectin antibodies, and soluble P-selectin inhibitors, e.g., soluble PSGL-1. As such, the present invention provides methods of treating an individual afflicted with a disease or disorder characterized by aberrant or unwanted hemostatic activity. In one embodiment, the method involves administering a modulator of P-selectin activity. In another embodiment, the method involves administering a soluble P-selectin polypeptide or a nucleic acid encoding a soluble P-selectin polypeptide to induce hemostasis and/or a procoagulant state.

(i) Methods for Inhibiting Soluble P-Selectin Expression, Synthesis, or Activity As discussed above, certain hemostatic disorders, e.g., thrombotic disorders, may result from an increased or excessive level of hemostatic activity. In such circumstances, hemostatic activity, e.g., thrombosis, may have a causative or exacerbating effect on the disease state. In such cases, a reduction in hemostasis or hemostatic activity may be achieved by reducing circulating levels of soluble P-selectin. As such, an inhibitor of P-selectin activity may be used in accordance with the invention to reduce hemostasis. Such compounds may include, but are not limited to, small organic molecules, peptides, antibodies, and the like.

For example, compounds can be administered that compete with endogenous ligand for a soluble P-selectin polypeptide. The resulting reduction in the amount of ligand-bound soluble P-selectin polypeptide will modulate hemostatic activity. Compounds that can be particularly useful for this purpose include, for example, soluble proteins or peptides, such as peptides comprising one or more of the extracellular domains, or portions and/or analogs thereof, of the P-selectin ligand, PSGL-1, including, for example, soluble fusion proteins such as Ig-tailed fusion proteins. (For a discussion of the production of Ig-tailed fusion proteins, see, for example, U.S. Pat. No. 5,116,964).

In one embodiment, an inhibitor of P-selectin activity which reduces or inhibits the translocation of P-selectin from cellular storage pools to the cell surface, or which reduce or inhibit the proteolytic cleavage of cell surface P-selectin, can be effective in reducing circulating soluble P-selectin levels, and thus modulating hemostatic activity. Alternatively, an inhibitor of P-selectin activity which reduces P-selectin gene expression (e.g., P-selectin gene transcription or translation), or the expression of an alternatively spliced isoform of P-selectin lacking the transmembrane domain, can be used to reduce hemostasis.

Further, antisense and ribozyme molecules which inhibit expression of the P-selectin selectin gene may also be used in accordance with the invention to inhibit hemostasis. Still further, triple helix molecules may be utilized in inhibiting soluble P-selectin activity.

The antisense nucleic acid molecules of the invention are typically administered to a subject or generated in situ such that they hybridize with or bind to cellular mRNA and/or genomic DNA encoding a P-selectin protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave P-selectin mRNA transcripts to thereby inhibit translation of P-selectin mRNA. A ribozyme having specificity for a P-selectin-encoding nucleic acid can be designed based upon the nucleotide sequence of a P-selectin cDNA. For example, a derivative of a Tetrahymena L-19 IVS RNA can be constructed in which the nucleotide sequence of the active site is complementary to the nucleotide sequence to be cleaved in a P-selectin-encoding mRNA (see, for example, Cech et al. U.S. Pat. No. 4,987,071; and Cech et al. U.S. Pat. No. 5,116,742). Alternatively, P-selectin mRNA can be used to select a catalytic RNA having a specific ribonuclease activity from a pool of RNA molecules (see, for example, Bartel, D. and Szostak, J. W. (1993) *Science* 261:1411-1418).

P-selectin gene expression can also be inhibited by targeting nucleotide sequences complementary to the regulatory region of the P-selectin gene (e.g., the P-selectin promoter and/or enhancers) to form triple helical structures that prevent transcription of the P-selectin gene in target cells (see, for example, Helene, C. (1991) *Anticancer Drug Des.* 6(6):569-84; Helene, C. et al. (1992) *Ann. N.Y. Acad. Sci.* 660:27-36; and Maher, L. J. (1992) *Bioassays* 14(12):807-15).

Antibodies that are both specific for the P-selectin protein and interfere with its activity may also be used to modulate or inhibit P-selectin activity. Such antibodies may be generated, using standard techniques, against the P-selectin protein itself or against peptides corresponding to portions of the protein. Such antibodies include but are not limited to polyclonal, monoclonal, Fab fragments, single chain antibodies, or chimeric antibodies.

In instances where the target gene protein is intracellular, e.g., localized in storage granules, and whole antibodies are used, internalizing antibodies may be preferred. Lipofectin liposomes may be used to deliver the antibody or a fragment of the Fab region which binds to the target epitope into cells. Where fragments of the antibody are used, the smallest inhibitory fragment which binds to the target protein's binding domain is preferred. For example, peptides having an amino acid sequence corresponding to the domain of the variable region of the antibody that binds to the target gene protein may be used. Such peptides may be synthesized chemically or produced via recombinant DNA technology using methods well known in the art (described in, for example, Creighton (1983), supra; and Sambrook et al. (1989) supra). Single chain neutralizing antibodies which bind to intracellular target gene epitopes may also be administered. Such single chain antibodies may be administered, for example, by expressing nucleotide sequences encoding single-chain antibodies within the target cell population by utilizing, for example, techniques such as those described in Marasco et al. (1993) *Proc. Natl. Acad. Sci. USA* 90:7889-7893).

In certain embodiments, antibodies that are specific for the extracellular domain of the P-selectin protein, for example, and that interfere with its activity, are particularly useful in modulating hemostasis. Such antibodies are especially efficient because they can access the target domains directly from the bloodstream. Any of the administration techniques described below which are appropriate for peptide administration may be utilized to effectively administer inhibitory P-selectin antibodies to their site of action.

Antibodies for the modulation of P-selectin function are disclosed in U.S. Pat. Nos. 6,033,667; 5,800,815; and 5,622,701.

The inhibitors of P-selectin, as described herein, may be administered alone or in conjunction with other agents, compounds, or compositions which are useful in reducing hemostasis or thrombosis, including, but not limited to, heparin, aspirin, and other anti-coagulants such as warfarin (Coumadin™), nicoumalone (Sintrom™), or anti-platelet aggregation agents such as inhibitors of αIIbβ3.

(ii) Methods for Restoring or Increasing P-Selectin Polypeptide Activity

Certain hemostatic disorders, e.g., hemorrhagic disorders, may result from an reduced level of hemostatic activity. Moreover, the progression of some vasculature-associated disorders is dependent on a blood supply to the disease site. In such circumstances, a reduction in or insufficient hemostatic activity, may have a causative or exacerbating effect on the disease state. In such cases, an increase in hemostasis or induction of a procoagulant state may be achieved by using an inducer of P-selectin activity to increase P-selectin activity, preferably by increasing circulating levels of soluble P-selectin.

Described in this section are methods whereby the level of soluble P-selectin activity may be increased to levels wherein the symptoms of hypocoagulation disorders or vasculature-associated diseases are ameliorated. The level of soluble P-selectin polypeptide activity may be increased, for example, by either increasing the level of P-selectin gene expression, e.g., an alternatively spliced isoform of P-selectin lacking the transmembrane domain, or by increasing the plasma level of active soluble P-selectin protein which is present.

For example, a soluble P-selectin polypeptide or fusion protein, at a level sufficient to ameliorate disease symptoms may be administered to a patient exhibiting such symptoms.

Any of the techniques discussed herein may be used for such administration. One of skill in the art will readily know how to determine the concentration of effective, non-toxic doses of the soluble P-selectin polypeptide, utilizing techniques such as those described herein.

Additionally, RNA sequences encoding a soluble P-selectin polypeptide may be directly administered to a patient exhibiting disease symptoms, at a concentration sufficient to produce a level of soluble P-selectin polypeptide such that disease symptoms are ameliorated. Any of the techniques discussed below, which achieve intracellular administration of compounds, such as, for example, liposome administration, may be used for the administration of such RNA molecules. The RNA molecules may be produced, for example, by recombinant techniques such as those described herein.

Further, subjects may be treated by gene replacement therapy. One or more copies of a gene encoding soluble P-selectin, or a soluble P-selectin fusion protein, that directs the production of a functional soluble P-selectin polypeptide or fusion protein, may be inserted into cells using vectors which include, but are not limited to adenovirus, adeno-associated virus, and retrovirus vectors, in addition to other particles that introduce DNA into cells, such as liposomes. Additionally, techniques such as those described above may be used for the introduction of soluble P-selectin gene sequences into human cells.

Cells, preferably, autologous cells, containing soluble P-selectin expressing gene sequences may then be introduced or reintroduced into the subject at positions which allow for the amelioration of disease symptoms.

In one embodiment, inducers of P-selectin activity which increase or enhance the translocation of P-selectin from cellular storage pools to the cell surface, or which increase or enhance the proteolytic cleavage of cell surface P-selectin, can be effective in increasing circulating soluble P-selectin levels, and thus modulating hemostatic activity. Alternatively, compounds which stimulate P-selectin gene expression (e.g., P-selectin gene transcription or translation), or the expression of an alternatively spliced isoform of P-selectin lacking the transmembrane domain, can be used to induce hemostasis. Furthermore, inducers of P-selectin activity which enhance P-selectin activity, e.g., a soluble P-selectin agonist, may be used in accordance with the invention to induce hemostasis. In another embodiment, inducers of P-selectin activity which mimic P-selectin activity may be used to modulate hemostatic activity. For example, an inducer of P-selectin activity, e.g., an antibody, which binds to and activates a P-selectin ligand or receptor on a cell can be used to modulate hemostasis. In one embodiment, an antibody against PSGL-1, preferably an activating antibody, binds to PSGL-1 on a cell and modulates hemostatic activity. In another embodiment, an inducer of P-selectin activity binds to a P-selectin ligand or receptor on a cell induces release of microparticles containing tissue factor.

Such inducers of P-selectin activity may include, but are not limited to, small organic molecules, peptides, antibodies, and the like.

Inducers of P-selectin activity, as described herein, may be administered alone or in conjunction with other anti-hemorrhagic or pro-coagulant agents, compounds or compositions, including, but not limited to Factor VIII, von Willebrand factor, platelets, the absorption analogue DDAVP, and fibrin, e.g., fibrin glue. In one embodiment, inducers of P-selectin activity as described herein may be administered to a patient suffering from, for example, hemophilia A or von Willebrand disease where antibodies to Factor VIII have been developed by the patient, thereby reducing the effectiveness of Factor VIII replacement therapy alone.

C. Pharmacogenomics

A modulators of P-selectin activity, for example, as identified by a screening assay described herein, or a soluble P-selectin polypeptide, can be administered to individuals to treat (prophylactically or therapeutically) hemostatic disorders associated with aberrant or unwanted hemostatic activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a modulator of P-selectin activity or a soluble P-selectin polypeptide, as well as tailoring the dosage and/or therapeutic regimen of treatment with a modulator of P-selectin activity, or a soluble P-selectin polypeptide.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11): 983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., P-selectin), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a soluble P-selectin polypeptide, or modulator thereof, of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a soluble P-selectin polypeptide or soluble P-selectin modulator.

VI. Screening Assays

The invention provides a method (also referred to herein as a "screening assay") for identifying modulators, i.e., candidate or test compounds or agents (e.g., peptides, peptidomimetics, small molecules (organic or inorganic) or other drugs) which modulate P-selectin activity, and which may thus be used to modulate hemostatic potential.

These assays are designed to identify compounds, for example, that bind to a P-selectin polypeptide, e.g., a soluble P-selectin polypeptide, bind to other proteins that interact with a P-selectin polypeptide, and modulate the interaction of a P-selectin polypeptide with other proteins, e.g., a P-selectin ligand, and thus modulate P-selectin activity. Screening assays can also be used to identify modulators of P-selectin activity, for example, that regulate P-selectin gene expression, the alternative splicing of the P-selectin gene encoding a soluble P-selectin isoform, the translocation of P-selectin from cellular storage pools to the cell surface, and the proteolytic cleavage of P-selection on the cell surface resulting in the release of soluble P-selectin. Moreover, screening assays can be used to identify inducers of P-selectin activity, for example, that mimic the activity of a P-selectin polypeptide, e.g., the binding of P-selectin to a P-selectin ligand or receptor, or the activity of P-selectin towards a P-selectin responsive cell. Such compounds may include, but are not limited to, peptides, antibodies, or small organic or inorganic compounds.

Compounds identified via assays such as those described herein may be useful, for example, for modulating hemostasis, and for treating hemostatic disorders and/or vasculature-associated diseases. In instances whereby a hemostatic disorder or a vasculature-associated disease results from an overall lower level of coagulation, useful compounds would bring about an effective increase in the level of P-selectin activity, e.g., an inducer of P-selectin activity. In other instances wherein a hemostatic disorder results from an overall increased level of coagulation or thrombosis, compounds that reduce the level of P-selectin activity would be beneficial, e.g., an inhibitor of P-selectin activity. Cell and animal models for testing the effectiveness of compounds identified by techniques such as those described in this section are discussed herein.

The test compounds can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In one embodiment, an assay is a cell-based assay comprising contacting a cell with a test compound and determining the ability of the test compound to modulate (e.g., induce or inhibit) P-selectin activity. For example, a cell expressing a P-selectin ligand or receptor, e.g., a leukocyte, is contacted with soluble P-selectin polypeptide either alone or in the presence of a test compound, and the ability of the test compound to modulate soluble P-selectin induced release of microparticles containing tissue factor is determined, as described herein. A similar cell-based assay could be used to identify a compound which mimics soluble P-selectin hemostatic activity, for example, by assaying the test compound for the ability to induce the release of microparticles containing tissue factor.

Furthermore, in another embodiment, a cell based assay can be used to determine the ability of the test compound to modulate the translocation of P-selectin to the cell surface, or to modulate the proteolytic cleavage of P-selectin from the cell surface. The presence of P-selection on the surface of a cell can be assessed by standard techniques, such as flow cytometry. The cleavage of P-selectin and concurrent release of soluble P-selectin selectin can be assessed by measuring the level of membrane-associated P-selectin as compared to the level of soluble P-selectin in the culture medium.

In a further embodiment, modulators of P-selectin activity are identified in a method wherein a cell is contacted with a candidate compound and the expression of soluble P-selectin mRNA or protein in the cell culture is determined by standard techniques. The level of expression of soluble P-selectin niRNA or protein in the presence of the candidate compound is compared to the level of expression of soluble P-selectin mRNA or protein in the absence of the candidate compound. The candidate compound can then be identified as a modulator of soluble P-selectin activity based on this comparison. For example, when expression of soluble P-selectin mRNA or protein is greater (statistically significantly greater) in the presence of the candidate compound than in its absence, the candidate compound is identified as a inducer of P-selectin activity. Alternatively, when expression of soluble P-selectin mRNA or protein is less (statistically significantly less) in the presence of the candidate compound than in its absence, the candidate compound is identified as an inhibitor of P selectin activity.

In another embodiment, the ability of a test compound to modulate soluble P-selectin binding to a receptor or ligand can also be determined, for example by coupling soluble P-selectin with a radioisotope or enzymatic label such that the binding of the soluble P-selectin can be determined by detecting labeled soluble P-selectin in a complex. For example, compounds (e.g., P-selectin polypeptides, P-selectin ligands) can be labeled with $^{125}I$, $^{35}S$, $^{14}C$, or $^{3}H$, either directly or indirectly, and the radioisotope detected by direct counting of radioemmission or by scintillation counting. Compounds can further be enzymatically labeled with, for example, horseradish peroxidase, alkaline phosphatase, or luciferase, and the enzymatic label detected by determination of conversion of an appropriate substrate to product.

Animal-based systems which act as models for hemostatic function or disease, such as the animal models described and exemplified herein, e.g., P-selectin deficient mice and vWF deficient mice, include, but are not limited to, non-recombinant and engineered transgenic animals. Models for studying vasculature-associated disease in vivo include animal models of tumorigenesis, tumor metastasis, and arteriosclerosis. Models for studying thrombotic disorders in vivo include animal models of thrombosis such as those described in, at least, for example, Leadley et al. (2000) *J Phannacol Toxicol Methods* 43:101, and Dorffler-Melly, et al. (2000) *Basic Res Cardiol* 95:503.

The animal-based model systems may be used in a variety of applications, for example, as part of screening strategies designed to identify compounds which are modulators of P-selectin activity. Thus, the animal-based models may be used to identify drugs, pharmaceuticals, therapies and interventions which may be effective in modulating hemostasis and treating hemostatic disorders and vasculature-associated diseases. For example, animal models may be exposed to a compound, suspected of exhibiting an ability to modulate P-selectin activity, and the response of the animals to the exposure may be monitored by assessing hemostatic activity before and after treatment. Hemostatic activity can be assessed using a clinically established test, e.g., a test of plasma clotting time, or using a method exemplified herein, e.g., fibrin formation in a perfusion chamber, plasma levels of soluble P-selectin and fibrinogen, hemorrhagic lesions in a local Schwartzman reaction, tissue factor activity.

In another aspect, the invention pertains to a combination of two or more of the assays described herein. For example, a modulator of P-selectin activity can be identified using a cell-based assay, and the ability of the agent to modulate P-selectin activity can be confirmed in vivo, e.g., in an animal such as an animal model for hemostasis or a hemostatic disorder.

This invention further pertains to novel agents identified by the above-described screening assays. Accordingly, it is within the scope of this invention to further test a modulator of P-selectin activity as described herein in an appropriate animal model for the ability to hemostatic potential. For example, an inducer or inhibitor of P-selectin activity can be used in an animal model to determine the LD50 and the ED50 in animal subjects, and such data can be used to determine the in vivo efficacy, toxicity, or side effects of treatment with such a potential modulator of hemostatic activity.

With regard to intervention, any treatments which modulate P-selectin activity and/or hemostatic potential should be considered as candidates for human therapeutic intervention. Dosages of test agents may be determined by deriving dose-response curves. Furthermore, this invention pertains to uses of newly identified modulators of P-selectin activity for modulating hemostasis, as described herein.

Additionally, gene expression patterns may be utilized to assess the ability of a compound, e.g., a modulator of P-selectin activity, to modulate hemostasis. For example, the expression pattern of one or more genes may form part of a "gene expression profile" or "transcriptional profile" which may be then be used in such an assessment. "Gene expression profile" or "transcriptional profile", as used herein, includes the pattern of mRNA expression obtained for a given tissue or cell type under a given set of conditions. Such conditions may include, but are not limited to, hemostatic disorders and/or vasculature-associated disease, including any of the control or experimental conditions described herein, for example, in a local Schwartzman reaction, or in an animal model of P-selectin deficiency or vWF deficiency. Gene expression profiles may be generated, for example, by utilizing a differential display procedure, Northern analysis and/or RT-PCR. In one embodiment, P-selectin gene sequences may be used as probes and/or PCR primers for the generation and corroboration of such gene expression profiles.

Gene expression profiles may be characterized for known states, either hemostatic disease or normal, e.g., within the animal-based model systems described herein. Subsequently, these known gene expression profiles may be compared to ascertain the effect a test compound has to modify such gene expression profiles, and to cause the profile to more closely resemble that of a more desirable profile.

For example, administration of a compound may cause the gene expression profile of a hemostatic disorder model system to more closely resemble the control system.

VI. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining P-selectin activity, e.g., soluble P-selectin expression in the context of a biological sample (e.g., blood, serum, cells, tissue) to thereby determine hemostatic activity, and to determine whether an individual is afflicted with a hemostatic disorder, or is at risk of developing a hemostatic disorder. The invention also provides for prognostic (or predictive) assays for determining whether an individual is manifesting a procoagulant state. Such assays can be used for prognostic or predictive purpose to modulate hemostasis, and thereby prophylactically treat an individual prior to the onset of a hemostatic disorder.

Another aspect of the invention pertains to monitoring the influence of agents (e.g., drugs, compounds) on hemostatic activity or procoagulant state in clinical trials.

These and other agents are described in further detail in the following sections.

A. Diagnostic Assays

The present invention encompasses methods for diagnostic and prognostic evaluation of hemostatic disease conditions, and for the identification of subjects exhibiting a predisposition to such conditions.

An exemplary method for detecting the presence or absence hemostatic activity in a biological sample involves obtaining a biological sample from a test subject and contacting the biological sample, e.g., a blood sample, with a compound or an agent capable of detecting P-selectin activity, e.g., a P-selectin binding substance that detects soluble P-selectin protein, such that the presence of P-selectin activity is detected in the biological sample.

A preferred agent for detecting soluble P-selectin protein is an antibody capable of binding to soluble P-selectin protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells and biological fluids isolated from a subject, as well as tissues, cells and fluids present within a subject. That is, the detection method of the invention can be used to detect P-selectin activity in a biological sample in vitro as well as in vivo. In vitro techniques for detection of P-selectin protein include enzyme linked immunosorbent assays (ELISAs), Western blots, immunoprecipitations and immunofluorescence. For a detailed explanation of methods for carrying out Western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

Detection of P-selectin activity can be accomplished, for example, by immunofluorescence techniques employing a fluorescently labeled antibody (see below) coupled with light microscopic, flow cytometric, or fluorimetric detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One means for labeling an anti-P-selectin polypeptide specific antibody is via linkage to an enzyme and use in an enzyme immunoassay (EIA) (Voller, "The Enzyme Linked Immunosorbent Assay (ELISA)", *Diagnostic Horizons* 2:1-7, 1978, Microbiological Associates Quarterly Publication, Walkersville, Md.; Voller, et al., J. Clin. Pathol. 31:507-520 (1978); Butler, Meth. Enzymol. 73:482-523 (1981); Maggio, (ed.) *Enzyme Immunoassay*, CRC Press, Boca Raton, Fla., 1980; Ishikawa, et al., (eds.) *Enzyme Immunoassay*, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Furthermore, in vivo techniques for detection of P-selectin protein include introducing into a subject a labeled anti-P-selectin antibody. For example, the antibody can be labeled with a radioactive marker whose presence and location in a subject can be detected by standard imaging techniques.

In one embodiment, the biological sample contains protein molecules from the test subject. A preferred biological sample is a blood sample isolated by conventional means from a subject (e.g., venipuncture).

Moreover, it will be understood that any of the above methods for detecting soluble P-selectin can be used to monitor the course of treatment or therapy.

In another embodiment, the methods further involve obtaining a control biological sample from a control subject, contacting the control sample with a compound or agent capable of P-selectin activity, e.g., soluble P-selectin, such that the presence of P-selectin activity is detected in the biological sample, and comparing the presence of P-selectin activity in the control sample with the presence of P-selectin activity in the test sample, to thereby assess hemostatic activity.

In one embodiment, an increased level of P-selectin activity is indicative of increased hemostatic activity, e.g., a procoagulant state. In another embodiment, a decreased level of P-selectin activity is indicative of decreased hemostatic activity, e.g., a hypocoagulable state.

B. Prognostic Assays

The diagnostic methods described herein can furthermore be utilized to identify subjects having or at risk of developing a hemostatic disorder e.g., a disorder associated with aberrant or unwanted hemostatic activity (i.e., a thrombotic disorder, a hemorrhagic disorder). As used herein, the term "aberrant" includes a level of hemostatic activity which deviates from clinically established normal levels of hemostatic activity under defined physiological conditions. Aberrant hemostatic activity includes increased or decreased hemostatic activity. As used herein, the term "unwanted" includes an unwanted phenomenon involved in a biological response such as hemorrhage or thrombosis. For example, the term unwanted includes hemostatic activity which is undesirable in a subject.

The assays described herein, such as the preceding diagnostic assays or the following assays, can be utilized to identify a subject having or at risk of developing a hemostatic disorder. Thus, the present invention provides a method for identifying a hemostatic disorder associated with aberrant or unwanted hemostatic activity in which a test sample is obtained from a subject and P-selectin activity is detected, wherein the presence of aberrant or unwanted P-selectin activity is diagnostic for a subject having or at risk of developing a hemostatic disorder. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a hemostatic disorder. For example, such methods can be used to determine whether a subject can be effectively treated with an agent for a hemorrhagic disorder or a thrombotic disorder. Thus, the present invention provides methods for determining whether a subject can be effectively treated with an agent for a hemostatic disorder, e.g., a disorder associated with aberrant or unwanted hemostatic activity, in which a test sample is obtained and P-selectin activity is detected (e.g., wherein the level of P-selectin activity is diagnostic for a subject that can be administered the agent to treat a hemostatic disorder).

Furthermore, any cell type or tissue in which P-selectin activity is expressed may be utilized in the prognostic assays described herein.

C. Monitoring of Effects During Clinical Trials

The present invention provides methods for evaluating the efficacy of drugs and monitoring the progress of patients involved in clinical trials for the treatment of hemostatic disorders.

Monitoring the influence of agents (e.g., drugs) on P-selectin activity can be applied not only in basic drug screening, but also in clinical trials. For example, the effectiveness of an agent determined by a screening assay as described herein to induce P-selectin activity can be monitored in clinical trials of subjects exhibiting decreased or insufficient hemostatic activity. Alternatively, the effectiveness of an agent determined by a screening assay to inhibit P-selectin activity can be monitored in clinical trials of subjects exhibiting increased hemostatic activity, e.g., thrombosis or a procoagulant state. In such clinical trials, P-selectin activity can be used as a "read out" or marker of hemostatic activity. In addition, the level of P-selectin activity may be used as a read out of a particular drug or agent's effect on a hemostatic activity.

In a preferred embodiment, the present invention provides a method for monitoring the effectiveness of treatment of a subject with an modulator of P-selectin activity (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of P-selectin activity in the preadministration sample; (iii) obtaining one or more post-administration samples from the subject; (iv) detecting the level of P-selectin in the post-administration samples; (v) comparing the level of P-selectin activity in the pre-administration sample with that in the post administration sample or samples; and (vi) altering the administration of the agent to the subject accordingly. For example, increased administration of an inducer of P-selectin activity may be desirable to increase P-selectin activity to higher levels than detected, i.e., to increase the effectiveness of the agent to promote hemostasis. Alternatively, increased administration an inhibitor of P-selectin activity may be desirable to lower P-selectin activity to lower levels than detected, i.e. to increase the effectiveness of the agent to downregulate hemostasis. According to such an embodiment, P-selectin activity may be used as an indicator of the effectiveness of an agent, even in the absence of an observable phenotypic response.

VII. Pharmaceutical Compositions

Active compounds for use in the methods of the invention can be incorporated into pharmaceutical compositions suitable for administration. As used herein, the language "active compounds" includes nucleic acid molecules encoding soluble P-selectin, soluble P-selectin proteins, and active fragments thereof, and anti-P-selectin antibodies. Active compounds also include modulators of soluble P-selectin activity, e.g., inducers and inhibitors, identified compounds that modulate P-selectin gene expression, synthesis, and/or activity, or compounds that mimic P-selectin activity, e.g., an anti-PSGL-1 antibody. Such compositions typically comprise the compound, nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, ophthalmic, and rectal administration, including direct installation into a disease site. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic. agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a inducer or inhibitor of P-selectin activity, a soluble P-selectin fusion protein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. In one embodiment, a "therapeutically effective dose" refers to that amount of an active compound sufficient to result in modulation of hemostasis or hemostatic potential. In another embodiment, a therapeutically effective dose refers to an amount of an active compound sufficient to result in amelioration of symptoms of a hemostatic disorder or a vasculature-associated disease. In yet another embodiment, a therapeutically effective dose refers to that amount of an active compound sufficient to modulate the level and/or activity of soluble P-selectin.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses active agents which modulate soluble P-selectin expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

In certain embodiments of the invention, a modulator of P-selectin activity is administered in combination with other agents (e.g., a small molecule), or in conjunction with another, complementary treatment regime. For example, in one embodiment, an inducer of P-selectin activity is used to treat a vasculature-associated disease. In the instance where the vasculature-associated disease is a tumor, the subject may be treated with an inducer of P-selectin activity, and further treated with a molecule effective to induce a procoagulant state in tumor associated vasculature, e.g., a molecule comprising a first binding region that binds to a component of a tumor cell or tumor associated vasculature (e.g., VCAM-1) operatively linked to a coagulation factor or a second binding region that binds to a coagulation factor, thereby increasing effectiveness of the treatment at the disease site. The vessels at the disease site in other vasculature-associated diseases may be similarly targeted with a coagulation factor or procoagulant agent, such that the specificity and effectiveness of the inducer of P-selectin activity is enhanced. In another embodiment, an inhibitor of P-selectin activity may be used in conjunction with anti-coagulant agents (e.g., integrin inhibitors, aspirin, heparin) in the treatment of thrombotic disorders, such as restenosis following medical intervention.

Further, an antibody (or fragment thereof) may be conjugated to a therapeutic moiety such as a cytotoxin, a therapeutic agent or a radioactive metal ion. The conjugates of the invention can be used for modifying a given biological response, and the drug moiety is not to be construed as limited to classical chemical therapeutic agents. For example, the drug moiety may be a protein or polypeptide possessing a desired biological activity. Such proteins may include, for example, a coagulation factor such as tissue factor; a protein such as vascular endothelial growth factor ("VEGF"), platelet derived growth factor, and tissue plasminogen activator; biological response modifiers such as, for example, lymphokines, cytokines and growth factors; or a toxin.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2$^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

This invention is further illustrated by the following examples which should not be construed as limiting. The contents of all references, patents and published patent applications cited throughout this application, as well as the Figures, are incorporated herein by reference.

EXAMPLES

Example 1

Hemostatic Potential in Animals with Increased Levels of Souluble P-Selectin

Transgenic mice that express P-selectin lacking the cytoplasmic domain (ΔCT mice) have been generated by gene replacement through homologous recombination in embryonic stem cells (Hartwell, D. W. et al. *J Cell Biol* (1998) 143:1129-1141). These mutant animals display an elevated level of soluble P-selectin in the plasma.

This example describes studies of the hemostatic potential in ΔCT mice as compared to wild type controls.

A. Fibrin Formation in a Perfusion Chamber

Fibrin formation of non-anticoagulated blood from wild type (WT), ΔCT mice, and P-selectin deficient (P-sel−/−) mice (Mayadas, T. N. et al. *Cell* (1993) 74:541-554) was compared ex vivo in a perfusion chamber. Leukocyte rolling and neutrophil extravasation, as well as hemostasis are compromised in these mice (Subramaniam, M. et al. *Blood* (1996) 87:1238-1242).

Briefly, glass capillary tubes (0.56 mm inner diameter) were coated with 1 mg/ml human fibrillar type III collagen (Sigma, St. Louis) as previously described (Andre, P. et al. *Arterioscler Thromb Vasc Biol* (1996) 16:56-63). Mice were anesthetized with 2.5% tribromoethanol (0.15 ml/10 g). Non-anticoagulated blood was collected directly from the vena cava of the mice using a butterfly 25 G, and perfused through the collagen coated perfusion chamber using silastic tubing. A flow rate of 220 μl/minute was established for 2 minutes by a syringe pump (Harvard Apparatus) mounted distal to the chamber, resulting in a shear rate of 212 s$^{-1}$, according to the equation: $\gamma=4Q/\pi r^3$. Immediately after the blood perfusion, the thrombotic deposits formed onto the collagen surface were rinsed for 20 seconds with PBS and fixed in an ice cold 2.5% cacodylate buffered glutaraldehyde (pH 7.4) at the same shear rate. The perfusion chamber was then removed from the flow system and fixed in a freshly prepared fixative buffer for 24 hours at 4° C. En face visualization of the thrombotic deposits was performed under light microscopy after epon embedding.

FIG. 1 is a photograph of en face examination of the thrombotic deposits formed after a 2 minute non-anticoagulated blood perfusion (blood flow, left to right). The white arrow indicates platelet rich thrombus; the black arrow indicates fibrin tail formed distally the platelet thrombus. As shown in FIG. 2, in 4 out of 11 perfusion chambers performed with wild type animals (one perfusion chamber per animal), a fibrin tail was found distally to the platelet aggregate. In 8 out of 9 perfusion chambers performed in ΔCT mice, a fibrin tail was present. In addition, the fibrin tail from the ΔCT mice was significantly longer than that observed in the wild type mice. None of the perfusion chambers performed with P-selectin deficient blood exhibited a fibrin tail. The statistical comparison between fibrin formation in the 3 genotypes was performed using the Log rank test. A Student's t test was used to compare the length of the fibrin tail.

B. Levels of Soluble P-Selectin and Fibrinogen in Plasma

The level of soluble P-selectin in plasma was measured using a modified sandwich ELISA procedure as previously described (Hartwell, D. W. et al. *J Cell Biol* (1998) 143:1129-

1141). Briefly, plasma samples of wild type (WT) and ΔCT mice were incubated for 2 hours at 37° C. with monoclonal anti-mouse P-selectin antibody (RB 40.34, Pharmingen Corp., San Diego, Calif.)-coated plates. After washing, a biotinylated rabbit anti-P-selectin antibody (Pharmingen Corp., San Diego, Calif.) was added to the wells and incubated for 2 hours. ExtrAvidin-conjugated alkaline phosphatase was added and the activity was revealed with p-nitrophenyl phosphate (Sigma Chemical Co., St Louis, Mo.). Plates were read at 405 nm in an Epson LX-300 ELISA reader (Dynatech Laboratories, Chantilly, Va.). The plasma level of fibrinogen was measured according to the Sigma Diagnostics Procedure No. 886 (St. Louis, Mo.) and expressed in mg/dL.

As shown in Table 1 below, a 3-fold increase in the level of soluble P-selectin was found in the plasma of ΔCT mice compared with wild type mice. In contrast, no significant difference was observed in the plasma fibrinogen levels in these animals.

TABLE 1

| | Soluble P-selectin in plasma | | | Fibrinogen level in plasma | |
|---|---|---|---|---|---|
| | (µg/ml) | n | | (mg/dl) | N |
| WT | 0.34 | 4 | WT | 367 ± 24 | 13 |
| ΔCT | 1.05 | 4 | ΔCT | 344 ± 14 | 13 |

C. Hemorrhagic Lesions in a Local Shwartzman Reaction

Local Shwartzman reaction is a hemorrhagic and necrotic lesion induced by endotoxin and cytokines, and is a prototypic model for the interrelation between the inflammatory and hemostatic systems. Briefly, 12 to 14 week old age-matched male wild type (WT) and ΔCT mice were primed on day 0 by a subcutaneous injection of *Escherichia coli* LPS 055:B5 (Difco Laboratories, Detroit, Mich.) at 100 µg/mouse in 0.1 ml of sterile phosphate buffered saline (PBS). Twenty four hours later (day 1), recombinant TNF-α (Genzyme, Cambridge, Mass.) at 0.3 µg/mouse was injected at the same skin site, as described (Subramaniam, M et al. *Blood* (1996) 87:1238-1242). On day 2, the hemorrhagic lesions were examined and scored on a scale of 0 to 4 without knowledge of the mouse genotypes. Hematoxylin-eosin stained paraffin sections were prepared from the lesion site and the degree of inflammatory cell infiltration as well as hemorrhage were scored microscopically, on a scale of 0 to 4.

Macroscopic and microscopic evaluation of the injection sites revealed that after 48 hours, the average size of the hemorrhagic lesions in ΔCT mice was about 50% of that in the wild type (see FIG. 3). A highly significant reduction of the hemorrhage was also observed in wild type animals perfused with soluble P-selectin-Ig (1 µg/g; Pharmingen Corp., San Diego, Calif.) injected 1 hour prior to TNFα challenge as compared to those injected with human IgG1 (Sigma Chemical Co., St Louis, Mo.).

D. Fibrin Deposition in a Local Shwartzman Reaction

Paraffin sections from the Shwartzman lesion site of wild type mice injected with human IgG1 or soluble P-selectin, as described above, were de-paraffinized, sequentially blocked with avidin D solution and biotin blocking solution (Vector, Burlingame, Calif. ), and then stained with a rabbit anti-human fibrinogen antibody (1:1000 dilution; A0080, Dako, Carpinteria, Calif.) which cross-reacts with mouse fibrin/fibrinogen. Sections were then sequentially treated with a biotinylated goat anti-rabbit secondary antibody (Zymed Laboratories Inc., South San Francisco, Calif.), and an ABC mix solution (Vector, Burlingame, Calif.). Development was done by treating the sections with an AEC substrate kit for horseradish peroxidase (Vector, Burlingame, Calif.). Sections were counterstained with hematoxylin for 5 minutes.

Figure 4:
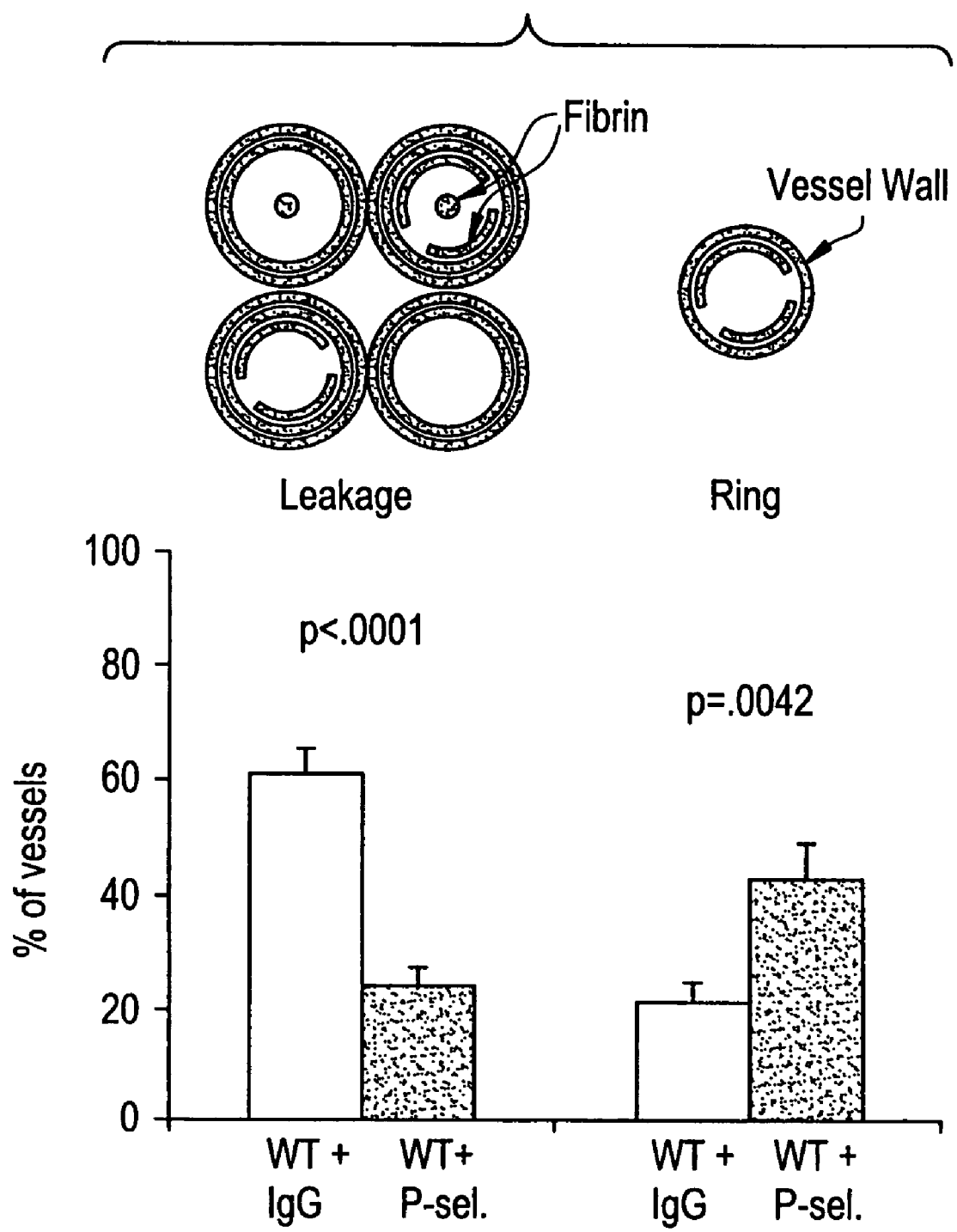
FIG. 4 shows fibrin deposition in a local Shwartzman reaction in wild type (WT) mice that were perfused with either human IgG1 or soluble P-selectin-Ig (P-sel).

All vessels which presented fibrin staining outside of the vessel wall were classified as "leakage". Vessels which presented fibrin staining on the luminal surface of the endothelial cells without fibrin outside the vessel wall were classified as "ring". The results are shown in FIG. 4. Wild type animals injected with soluble P-selectin exhibited a significant decrease in the percentage of "leakage" vessels, and an increase in the percentage of "ring" vessels, as compared with animals perfused with human IgG1.

E. Plasma Clotting Time

The plasma clotting time of wild type mice, either untreated, or infused with either human IgG1 (control) or soluble P-selectin (s-P-sel), P-selectin deficient, and ΔCT mice, either untreated or infused with human recombinant PSGL-1 (r-PSGL-1), was determined as follows. Briefly, 1 ml of blood was drawn from the retro-orbital venous plexus using plain microhematocrit capillary tubes and collected into polypropylene tubes containing 10% final volume of acid-citrate-dextrose (ACD: 38 mM citric acid, 75 mM trisodium citrate, 100 mM dextrose). Platelet poor plasma was prepared by centrifugation at 1,500 g for 25 minutes, followed by centrifugation at 15,000 g for 2 minutes to remove any contaminating cells from the plasma. Plasma clotting time was induced under stirring conditions (800 rpm) at 37° C. in an aggregometer by adding an equal volume of pre-warmed 20 mM $CaCl_2$ solution to the plasma in a siliconized tube.

Figure 5A:
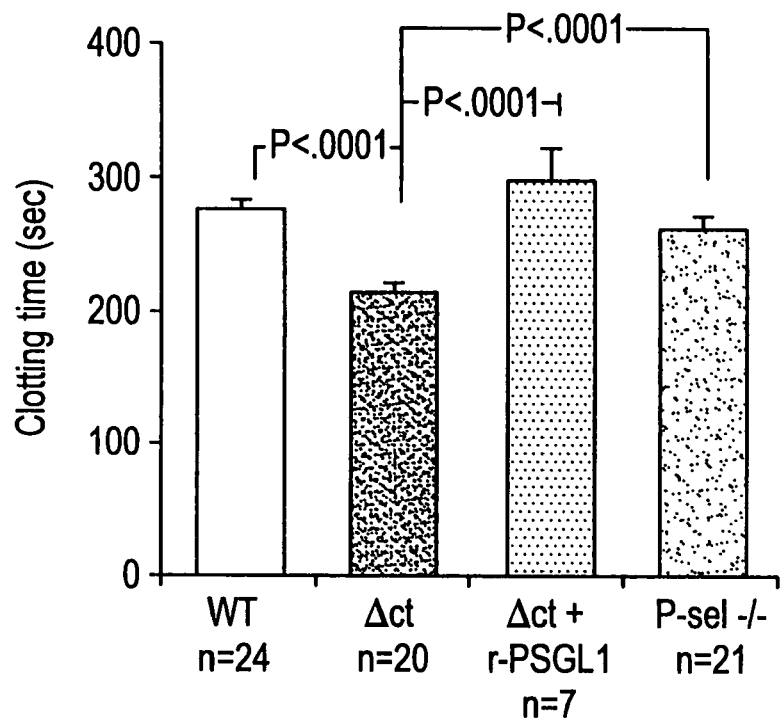
FIGS. 5A and B show the plasma clotting time of wild type mice (WT), P-selectin deficient mice (P-sel–/–), and ΔCT mice that were either untreated or perfused with recombinant PSGL-1 or recombinant soluble P-selectin.
Figure 5B:
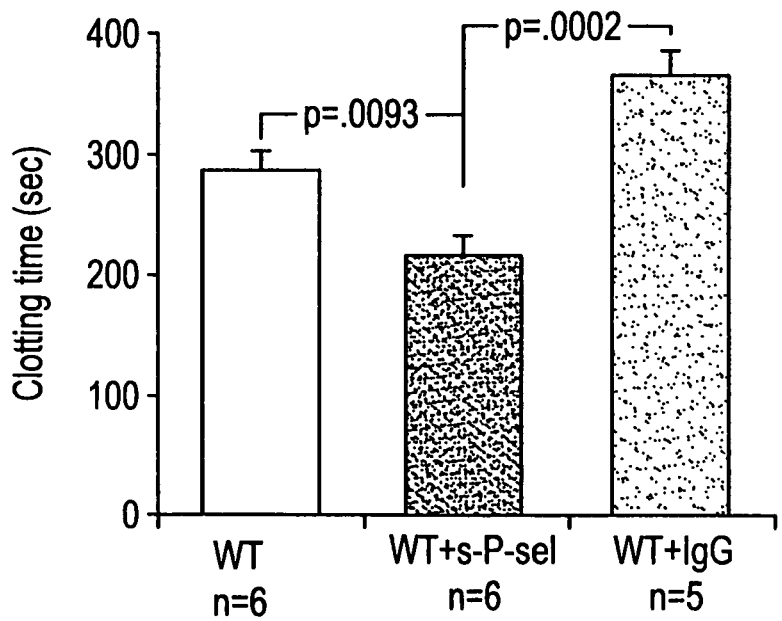

As shown in FIG. 5, ΔCT mice presented a significant reduction of the clotting time compared with wild type mice. In addition, a significant increase of the clotting time was observed on day 4 in ΔCT mice injected intravenously (on days 0 and 2) with human recombinant PSGL-1 IgG (10 mg/kg). In contrast, injection of soluble P-selectin in wild type mice significantly reduced the clotting time compared with the IgG treated control group.

F. Microparticles in Mouse Plasma

The levels of microparticles circulating in vivo in wild type mice, untreated, or infused with either human IgG1 (control) or soluble P-selectin (s-P-sel), and in ΔCT mice was determined as follows. Briefly, platelet poor plasma was prepared as described above. Subsequently, 300 µl of platelet poor plasma was collected per mouse, and three samples of platelet poor plasma from mice of the same genotype were pooled together, diluted 1:3 with buffer (10 mmol/L HEPES, 5 mmol/L KCl, 1 mmol/L $MgCl_2$, 136 mmol/L NaCl, pH 7.4), and centrifuged for 1.5 hours at 100,000 g. The supernatant was discarded and the pellet of microparticles was resuspended in a fixed volume (120 µl) of the same buffer.

Flow cytometric analysis was performed on a Becton-Dickinson FACSCalibur (Franklin Lakes, N.J.,) with CellQuest software (Becton-Dickinson, San Jose, Calif.). The light scatters and fluorescent channels were set at logarithmic gain (forward scatter was E00 with a threshold of 12 and sideward scatter was 300). To count the total population of microparticles, 30 µl aliquots were incubated for 15 minutes in the dark with calcein AM (0.25 µg/ml; Molecular Probes, Eugene, Oreg.). The total number of events were counted for a set interval of 10 seconds.

Figure 6:
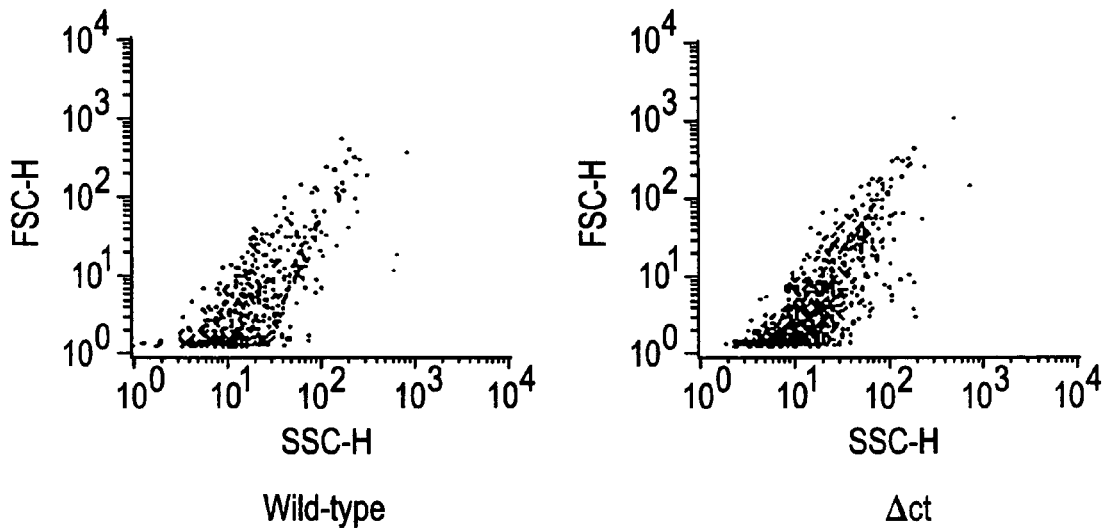
FIG. 6 shows the levels of microparticles in the circulation of wild type mice (WT) that were either untreated, perfused with human IgG1, or perfused with soluble P-selectin-Ig (s-P-sel), and ΔCT mice.

FIG. 6 shows that the number of microparticles was increased by 1.9-fold in ΔCT mice compared with wild type animals. Furthermore, a 2.7-fold increase in microparticles was obtained when wild type mice were injected intravenously with soluble P-selectin-Ig, as compared to human IgG1.

To identify the origin of the procoagulant activity, microparticle samples were stained for 20 minutes at room temperature with a sheep anti-rabbit tissue factor IgG (American Diagnostica Inc., Greenwich, CT) which recognizes mouse tissue factor (5 µg/ml final concentration). A FITC-conjugated rabbit anti-sheep IgG (1:1000 dilution; Zymed Laboratories Inc., South San Francisco, Calif.) was used as a secondary antibody. As controls, an identical concentration of control IgG antibodies were used (rat IgG, Sigma Chemical Co., St. Louis, Mo.; FITC-conjugated sheep IgG, Caltag Laboratories, Burlingame, Calif.). The microparticles were analyzed by flow cytometry.

FIG. 7 shows that there are an increased number of microparticles expressing tissue factor in the plasma of ΔCT mice.

G. Treatment of ΔCT Mice with Soluble PSGL-IG

Soluble PSGL-Ig infusion decreases the pro-coagulant phenotype of ΔCT mice as shown by a significant decrease in the number of microparticles and a prolonged clotting time of plasma. Infusion of control Ig had no such effect.

Plasma clotting time was determined as described above. For analysis of microparticles in plasma of ΔCT mice treated with PSGL-Ig, 200 µl of blood was collected by retro-orbital puncture on day 0. Platelet-poor plasma was obtained, and 40 µl was diluted in 260 µl PBS and immediately analyzed for microparticle number by FACS. Mice were then infused i.v. (days 0 and 2) with 10 mg/kg PSGL-Ig or control Ig. On day 4, 200 µl of blood was collected from the other eye, and the number of microparticles was determined.

Figure 11B:
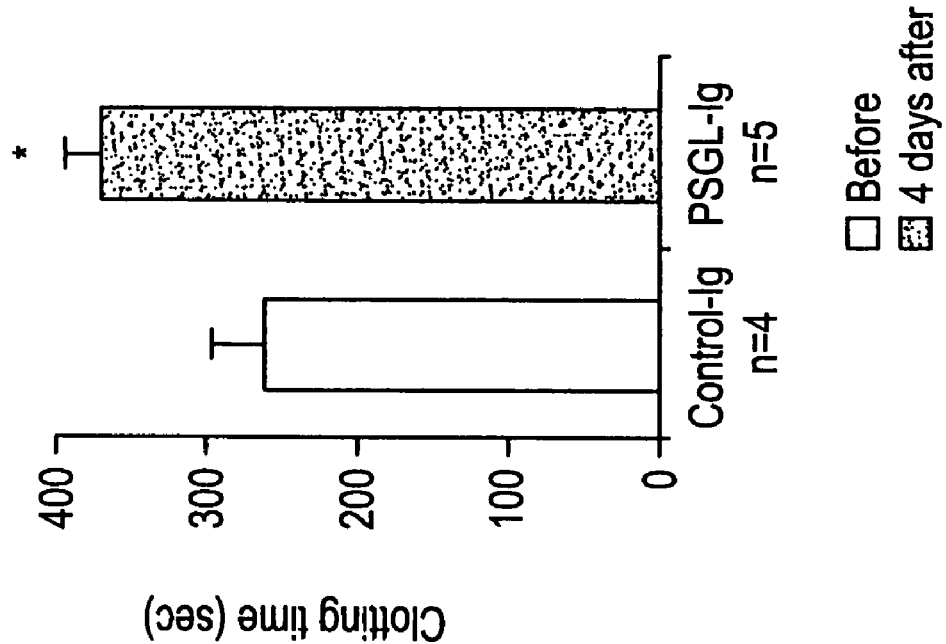
FIG. 11B shows the increase in clotting time after treatment of ΔCT mice with soluble PSGL-Ig as compared to control human Ig (*=p<0.05).
Figure 11A:
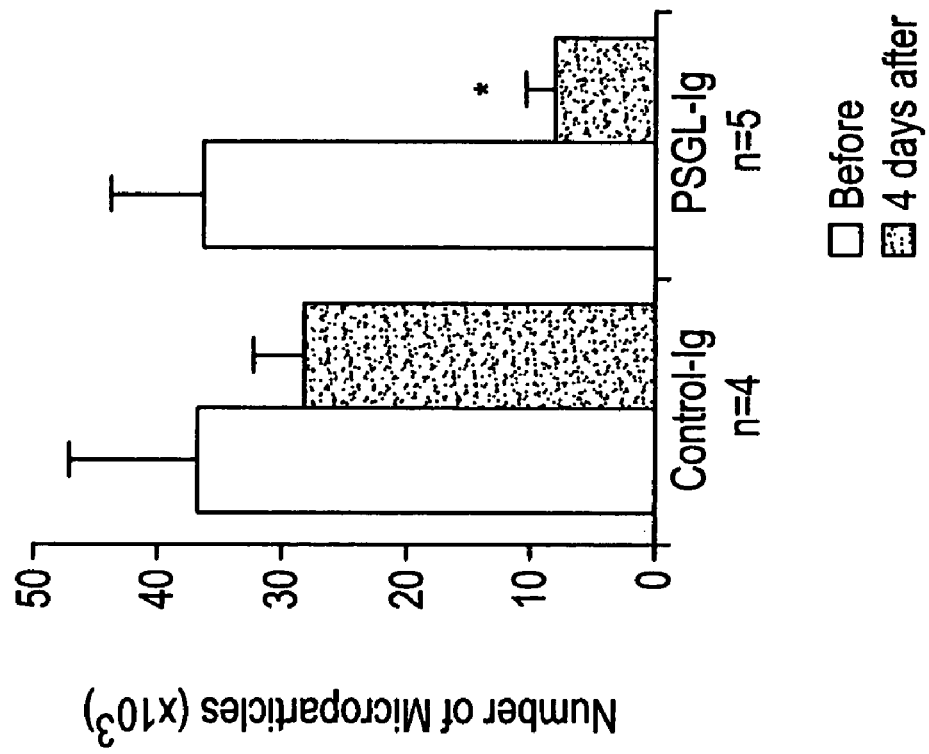
FIG. 11A shows the reduction in the number of microparticles after treatment of ΔCT mice with soluble PSGL-Ig as compared to control human Ig (*=p<0.05).

FIG. 11A shows the number of microparticles present in 40 µl of ΔCT plasma, before (open bars) and after (filled bars) two infusions of PSGL-Ig and control Ig in ΔCT mice (*=p<0.05).

FIG. 11B shows that the clotting time at the end of the experiment (e.g., after 4 days) was significantly longer in mice treated with soluble PSGL-Ig (filled bar) than in control Ig treated group (open bar) (*=p<0.05). These data show that inhibition of soluble P-selectin decreases the pro-coagulant state in vivo.

Example 2

Activity of Souluble P-Selection in Von Willebrand Factor Deficient Mice and Mice with Hemophilia A von Willebrand factor (vWF) deficient mice have only about 20% of the wild type level of factor VIII (anti-hemophilia factor), and thus have difficulty making fibrin clots (Denis, C. et al. *Proc Natl Acad Sci USA* (1998)95:9524-9529). Mice with hemophilia A are lacking factor VIII completely (Bi, L. et al. (1995) *Nature Genetics* 10:119-121. This example describes the hemostatic activity of soluble P-selectin in these animals.

A. Tissue Factor Activity in Platelet Poor Plasma

Platelet poor plasma was prepared from pooled plasma of vWF deficient mice (vWF−/−) infused with soluble P-selectin-Ig (n=2) or IgG1 (control; n=3). Microparticles were prepared by repeated centrifugation of platelet poor plasma. Briefly, the first centrifugation step at 12,000 g for 2 minutes was performed to remove any contaminating cells. The supernatant was then diluted in a 20 mM HEPES, 1 mM EDTA, pH7.2 solution and ultracentrifuged at 200,000 g for 90 minutes. The supernatant was discarded, and the pelleted microparticles were resuspended (½ of the initial volume) in a 10 mM HEPES, 136 mM NaCl, pH7.4 solution. Determination of tissue factor activity of the microparticle solution was measured through its ability to promote the activation of factor X (150 nM) by factor VIIa (5 nM) in the presence of 1 mM $CaCl_2$. The reaction was allowed to proceed for 20 minutes at 37° C. and was stopped by the addition of an excess of EDTA (5 mM final concentration). A chromogenic substrate of factor Xa, Spectrozyme® fXa, was added at a final concentration of 0.3 mM. The change in absorbance at 405 nm versus time was immediately recorded using a plate reader equipped with kinetics software (DYNEX Technologies, Inc.). The linear changes in absorbance directly correlate with the concentration of factor Xa generated in the assay.

As shown in Table 2 below, the tissue factor activity of the solution of microparticles from vWF deficient mice infused with soluble P-selectin-Ig was 2.1 fold higher than that of control mice infused with IgG1.

TABLE 2

| Tissue Factor (Xa) Activity in OD/minute | |
|---|---|
| vWF −/− +IgG1 | vWF −/− + soluble P-selectin-Ig |
| 2.54 | 5.26 |

B. Procoagulant Microparticle Generation by Infusion of Soluble P-Selectin-Ig

Figure 8:
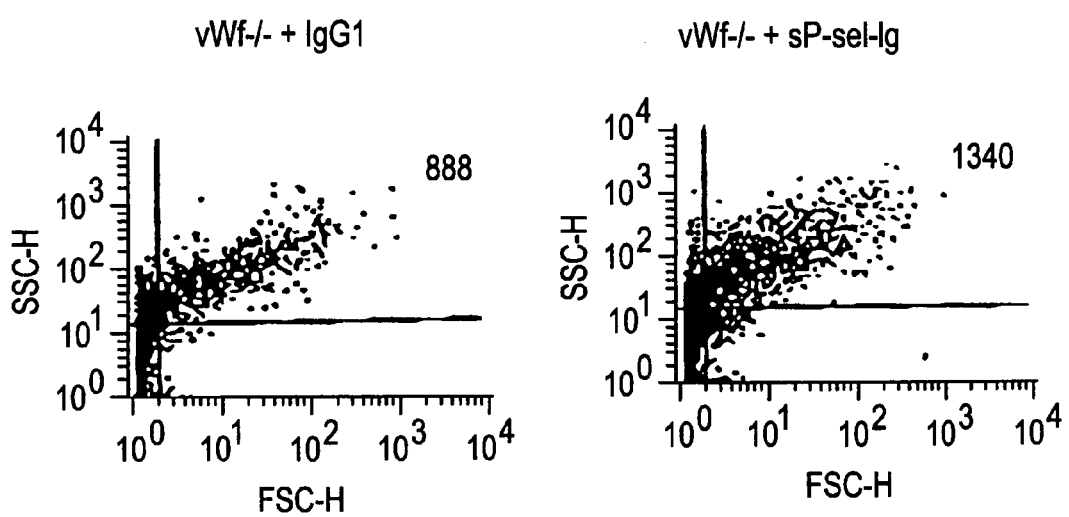
FIG. 8 shows the increased generation of procoagulant microparticles in the circulation of von Willebrand factor deficient mice (vWF–/–) that were perfused with soluble P-selectin-Ig (sP-sel-Ig).

The levels of microparticles circulating in vivo in vWF deficient mice, infused with either human IgG1 (control) or soluble P-selectin-Ig (sP-sel-Ig) was determined as described above. FIG. 8 shows that the number of microparticles was increased when vWF deficient mice were injected intravenously with soluble P-selectin-Ig, as compared to human IgG1 (control).

C. Prothrombin Clotting Time

Prothrombin clotting time (PT) is a global coagulation screening test. It involves extrinsic pathway of coagulation starting with activation of TF-VII(a) complex. PT time is measured in prewarmed (37° C.) platelet poor plasma after adding thromboplastin as a source of tissue factor, and $Ca^{2+}$.

Diluted prothrombin time was measured when pooled platelet poor plasma sample (0.1 ml) was mixed with 0.2 ml of diluted rabbit brain thromboplastin (IL TEST PT). Clotting time was determined using photometry detection of the first fibrin threads formed. FIG. 9 shows a prolonged prothrombin clotting time in vWF deficient plasma (vWF−/−) compared with wild type (wt) when the thromboplastin concentration decreased. This can be explained by the 20% of normal level of factor VIII found in the vWF deficient mice.

Clotting time of vWF deficient mice infused with either soluble P-selectin-Ig or IgG1 (control) was tested at the high dilution of thromboplastin (1:20,000) because it is known that at that dilution, prothrombin clotting time is preferentially tissue factor dependent. The infusion of soluble P-selectin-Ig in vWF deficient mice shortened the prothrombin clotting time by 28% when compared with vWF deficient mice infused with IgG1.

D. Bleeding Time

Bleeding time was measured as described by Dejana, et al. (1979) *Thromb. Res.* 15:199-201. Briefly, factor VIII-deficient mice were injected with 1.2 µg soluble P-selectin-Ig (P-sel-Ig) or human IgG1 control per gram of mouse. Six hours later mice were put in a restrainer, and a distal 3-mm segment of the tail was severed with a razor blade. The tail was immediately immersed in 0.9% isotonic saline at 37° C.

with the tip of tail 5 cm below the body. The bleeding time was defined as the time required for the stream of blood to cease. The infusion of soluble P-selectin reduced bleeding time in hemophilia A mice (factor VIII-deficient mice).

As shown in FIG. 10, bleeding time was significantly decreased for hemophilia A mice treated with soluble P-selectin-Ig as compared to hemophilia A mice treated with human IgG1.

E. Activated Partial Thromboplastin Time (APTT)

Activated partial thromboplastin time (APTT) is a global coagulation screening test. It involves the intrinsic pathway of coagulation.

The effect on soluble P-selectin on activated partial thromboplastin time and plasma clotting time in factor VIII-deficient mice (hemophilia A mice) was determined as follows. Briefly, hemophilia A mice were treated with 1.2 µg/g body weight P-selectin-Ig or human IgG1. Mice were bled into ACD six hours after perfusion. Platelet poor plasma was prepared as described above. Activated partial thromboplastin time (APTT) was determined with APTT reagent and clotting was initiated by addition of calcium ions. APTT and plasma clotting time are reduced in soluble P-selectin-Ig treated hemophilia A mice.

Figure 14A:
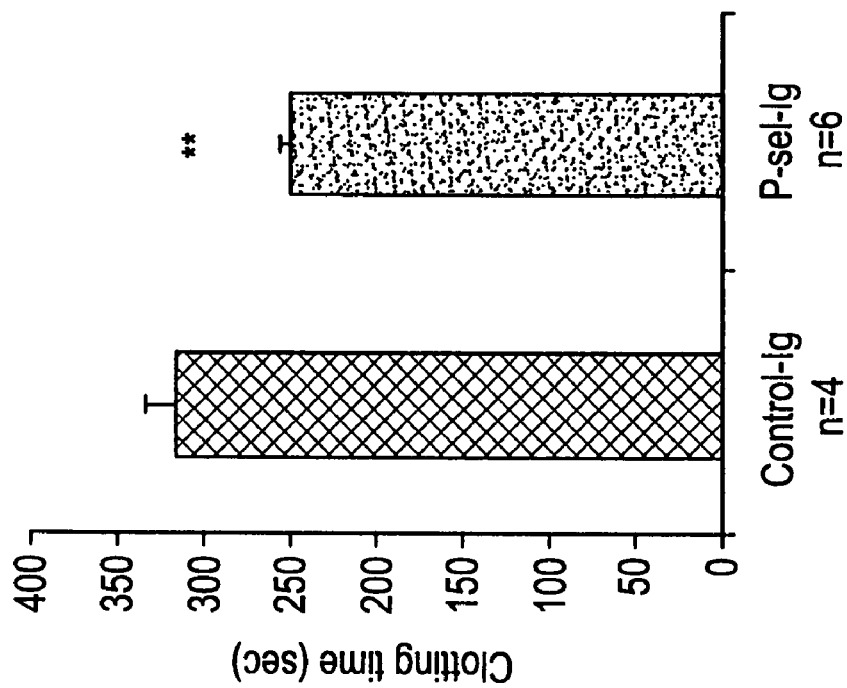
FIG. 14A shows activated partial thromboplastin time (APTT) in factor VIII–/– mice (hemophilia A mice) treated with control Ig or soluble P-selectin-Ig.
Figure 14B:
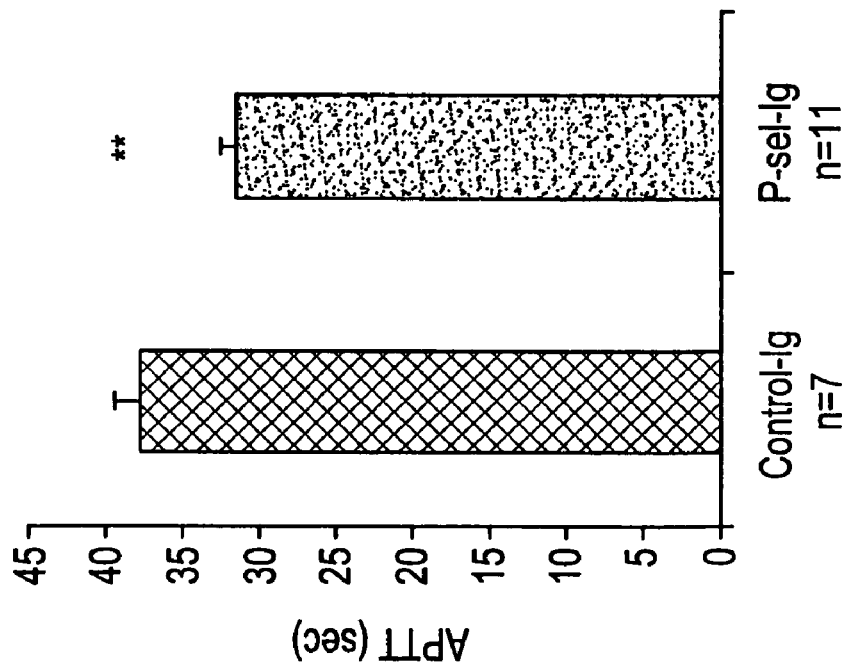
FIG. 14B shows plasma clotting time in factor VII–/– mice (hemophilia A mice) treated with control Ig or soluble P-selectin-Ig.

As shown in FIG. 14, APTT in soluble P-selectin-Ig treated hemophilia A mice was shorter as compared to mice treated with human IgG1 ($p<0.0013$, determined by unpaired t test). Recalcified clotting time of plasma of hemophilia A mice treated with soluble P-selectin-Ig was significantly reduced ($p<0.0058$, determined by unpaired t test) as compared to mice treated with control IgG1.

The foregoing Examples demonstrate the hemostatic activity of soluble P-selectin. The infusion of soluble P-selectin into a mouse induces a procoagulant state in the animal. When such an animal is wounded, fibrin is deposited more rapidly at the site of the vessel injury thus reducing leakage from the blood vessels. The plasma of the animal infused with soluble P-selectin clots faster. Transgenic animals expressing higher levels of soluble P-selectin (ΔCT mice) also form fibrin more readily than wild-type animals and are protected from excessive leakage in hemorrhagic injury. In contrast, animals lacking all forms of P-selectin have an increased hemorrhagic response and slightly longer bleeding time than wild type. These data indicate that the level of soluble P-selectin is a predictor of coagulation potential in a mammal.

Moreover, we have observed that infusion of soluble P-selectin into a mouse increases the numbers of microparticles containing tissue factor in the blood. Similarly, transgenic mice expressing higher than normal levels of soluble P-selectin have more tissue factor-containing microparticles in circulation. Infusion of soluble PSGL-1 (a ligand/inhibitor of P-selectin) reduces the numbers of tissue factor-containing microparticles and prolongs clotting time of the plasma in these mice. Thus, modulating P-selectin activity by, for example, modulating levels of soluble P-selectin can either increase or decrease hemostatic potential in a subject, and thus is useful for the diagnosis and treatment of hemostatic disorders.

Example 3

Soluble P-Selectin Generates Microparticles in Human Blood

An in vitro system was developed to further demonstrate how soluble P-selectin induces pro-coagulant activity. Generation of microparticles after the addition of 15 µg/ml of human P-selectin-Ig chimera or control human IgG1 was determined as described herein. Human blood was collected in ACD. The blood samples from four donors, each treated separately, were incubated at 37° C. Samples were handled under aseptic conditions to avoid LPS contamination. The generation of microparticles was analyzed by flow cytometry in platelet poor plasma diluted in PBS. Forward scatter and sideward scatter plot was used for the quadrant analysis to quantify the newly formed large procoagulatnt microparticles. Tissue factor positive microparticles were analyzed by flow cytometry. The microparticles were stained with a FITC-conjugated mouse anti-human tissue factor (American Diagnostica™).

Figure 12A:
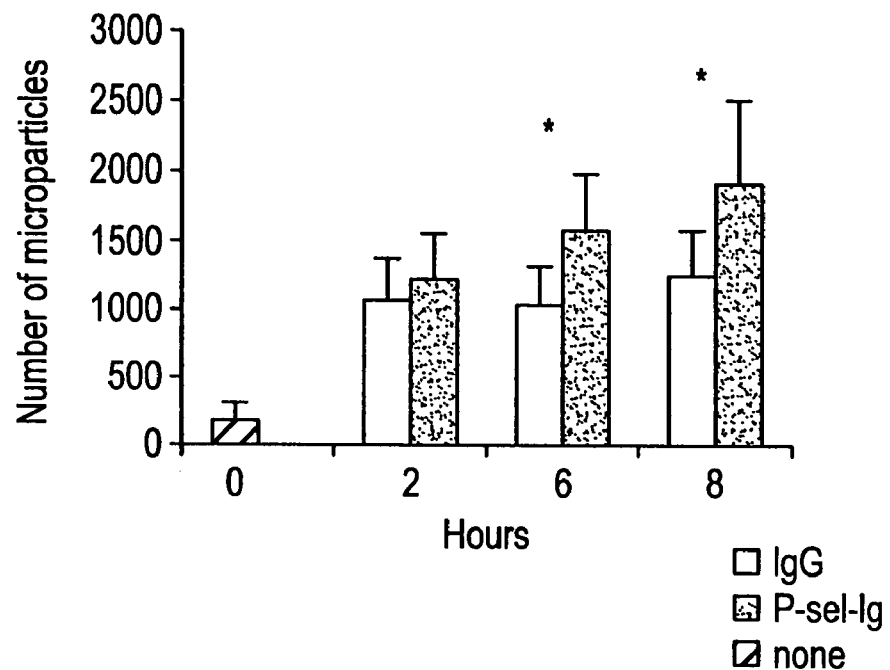
FIG. 12A shows the generation of procoagulant microparticles in human blood after incubation with either human IgG or soluble P-selectin-Ig (P-sel-Ig). After 6 hrs. incubation with soluble P-selectin-Ig, the numbers of microparticles significantly increased by 30% (*=p<0.04).

As shown in FIG. 12A, after 6 hours incubation with soluble P-selectin, the numbers of procoagulant microparticles were increased by 30% as compared to human IgG control (*=$p<0.04$).

Figure 12B:
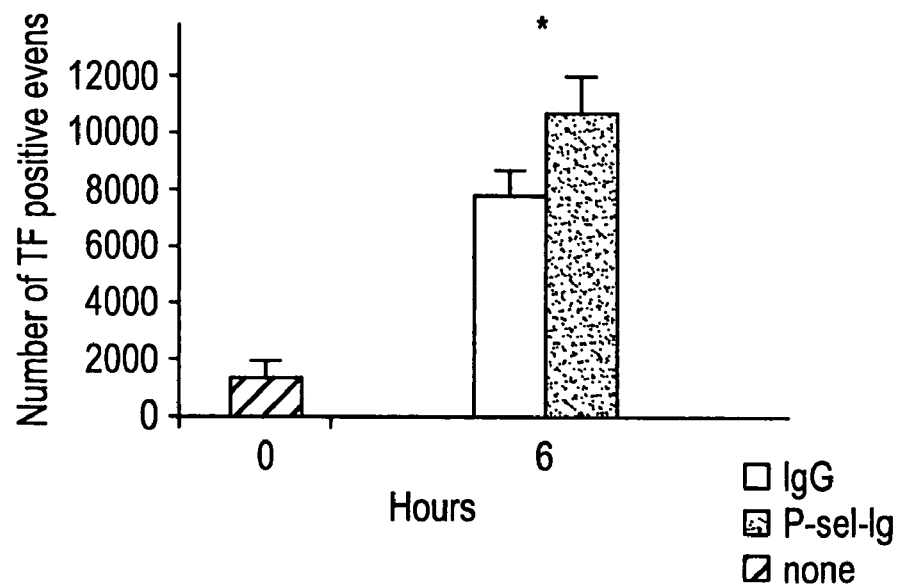
FIG. 12B shows the generation of tissue factor positive microparticles in human blood after incubation with either human IgG or soluble P-selectin-Ig (P-sel-Ig). The number of tissue factor positive evens was significantly increased at 6 hours by incubation with P-selectin Ig, 30% (*=p<0.05).

As shown in FIG. 12B, the number of tissue factor positive evens was significantly increased by incubation with soluble P-selectin-Ig in 6 hours by 30% (*=$p<0.05$).

Example 4

Souluble P-Selectin Shortens Whole Blood and Plasma Clotting Time in Human Blood Whole blood recalcified clotting time and plasma recalcified clotting time in human blood after the addition of 15 µg/ml of human P-selectin-Ig chimera or control human IgG1 was determined as follows. The human blood was collected in ACD. The blood samples from four donors, each treated separately, were incubated at 37° C. Samples were handled under aseptic conditions to avoid LPS contamination. The whole blood clotting time was measured in siliconized tubes in a Soloclot Coagulation and Platelet Analyzer (Sienco™).

Figure 13A:
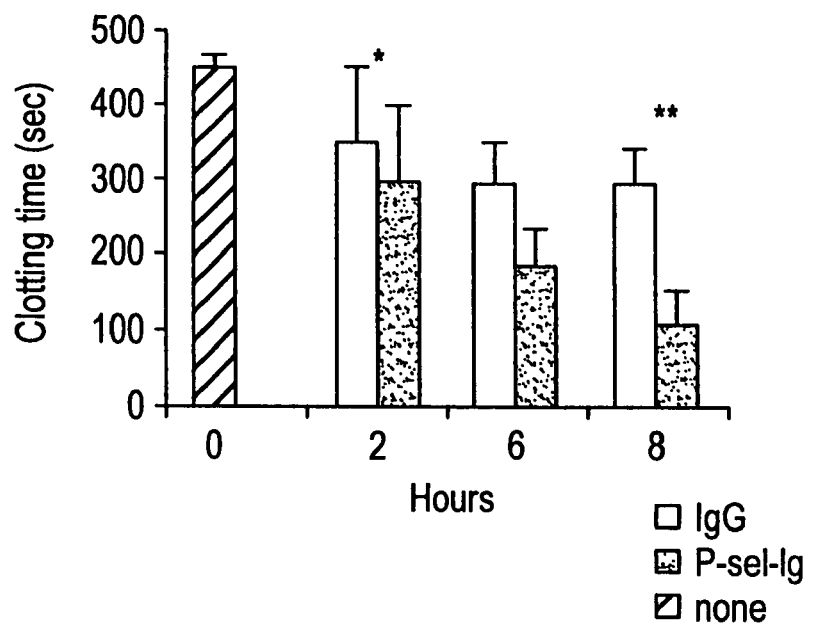
FIG. 13A shows the clotting time of human whole blood after incubation with human IgG or soluble P-selectin-Ig (P-sel-Ig). The clotting time of whole blood incubated with soluble P-selectin-Ig was shortened by about 20% after 2 hours (*=p<0.02) and by 60% after 8 hours of incubation (**=p<0.004).

As shown in FIG. 13A, the whole blood clotting time of human blood incubated with soluble P-selectin was shortened by about 20% after 2 hours (*=$p<0.02$) and by 60% after 8 hours of incubation (**=$p<0.004$) as compared to blood treated with IgG.

Figure 13B:
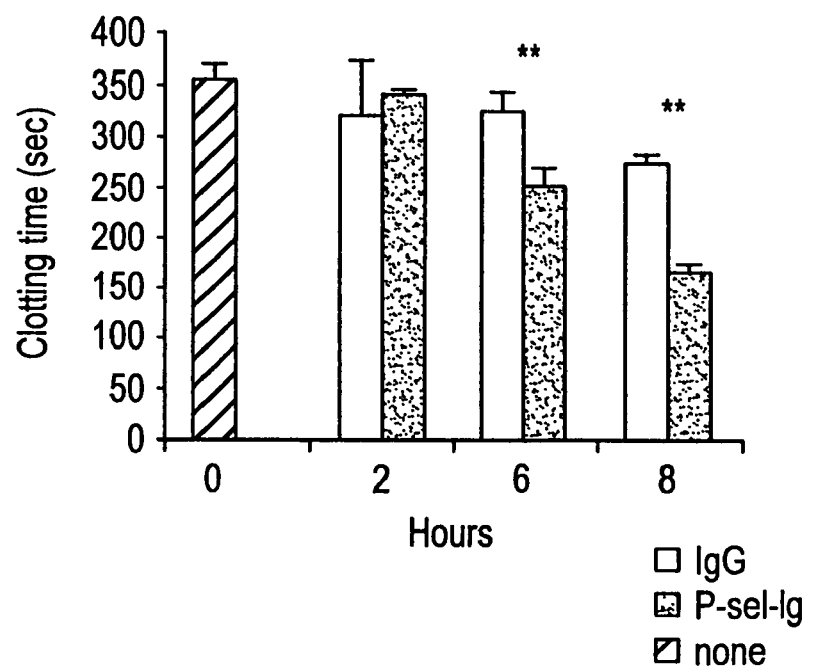
FIG. 13B shows the clotting time of human plasma after incubation with human IgG or soluble P-selectin-Ig (P-sel-Ig). The plasma clotting time of the soluble P-selectin treated blood was shortened by 25% after 6 hours of incubation and by 40% after 8 hours (** p<0.004).

As shown in FIG. 13B, the plasma clotting time of the soluble P-selectin blood was shortened by 25% after 6 hours of incubation and by 40% after 8 hours of incubation. (**$p<0.004$) as compared to control IgG and untreated plasma.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating hemophilia or von Willebrand's disease in a subject, said method comprising administering to said subject an inducer of P-selectin activity selected from the group consisting of a soluble P-selectin polypeptide and a P-selectin fusion protein, such that the hemophilia or von Willebrand's disease is treated or prevented.

2. The method of claim 1, wherein said hemophilia is hemophilia A.

3. The method of claim 1, wherein said hemophilia is hemophilia B.

4. The method of claim 1, wherein the inducer of P-selectin activity increases the level of soluble P-selectin polypeptide in the plasma of the subject.

5. The method of claim 1, wherein the inducer of P-selectin activity is a fusion protein.

6. The method of claim 1, wherein the P-selectin fusion protein comprises a soluble P-selectin polypeptide operatively linked to an immunoglobulin.

7. The method of claim 6, wherein the immunoglobulin is a human IgG 1, and the Fc region of the immunoglobulin is fused to the C-terminus of at least one soluble P-selectin polypeptide.

* * * * *